United States Patent
Ackermann et al.

(10) Patent No.: US 7,077,806 B2
(45) Date of Patent: Jul. 18, 2006

(54) ADAPTIVE INTERACTIVE PRECEPTORED TEACHING SYSTEM INCORPORATING REMOTE IMAGE MONITORING

(75) Inventors: Ralf W. Ackermann, Lyngby (DK); Henrik Aspe, Fredensborg (DK); Geoffrey S. Gates, Jacksonville, FL (US)

(73) Assignees: Novo Nordisk A/S, Bagsvaerd (DK); Mayo Medical Ventures, Rochester, MN (US)

( * ) Notice: Subject to any disclaimer, the term of this patent is extended or adjusted under 35 U.S.C. 154(b) by 748 days.

(21) Appl. No.: 10/028,540

(22) Filed: Dec. 19, 2001

(65) Prior Publication Data

US 2002/0188477 A1 Dec. 12, 2002

Related U.S. Application Data

(63) Continuation-in-part of application No. 09/877,492, filed on Jun. 8, 2001.

(51) Int. Cl.
*A61B 5/00* (2006.01)

(52) U.S. Cl. .................. 600/300; 434/118; 434/127; 128/904; 128/920

(58) Field of Classification Search ......... 600/300–301, 600/316, 322, 345, 347, 365, 587, 595; 128/903–905, 128/920–921, 897; 434/118, 219, 236–238, 434/262, 322–323, 350–354, 127; 705/1–4
See application file for complete search history.

(56) References Cited

U.S. PATENT DOCUMENTS

| | | | | |
|---|---|---|---|---|
| 5,019,974 A | * | 5/1991 | Beckers | 600/316 |
| 5,701,904 A | * | 12/1997 | Simmons et al. | 600/301 |
| 5,772,586 A | * | 6/1998 | Heinonen et al. | 600/300 |
| 5,840,020 A | * | 11/1998 | Heinonen et al. | 600/309 |
| 5,867,821 A | | 2/1999 | Ballantyne et al. | |
| 5,879,163 A | * | 3/1999 | Brown et al. | 434/236 |
| 5,924,074 A | | 7/1999 | Evans | |
| 5,940,802 A | | 8/1999 | Hildebrand et al. | |
| 5,954,641 A | | 9/1999 | Kehr et al. | |
| 6,014,631 A | | 1/2000 | Teagarden et al. | |

(Continued)

OTHER PUBLICATIONS

Memo from Dr. Geoffrey S. Gates of Mayo Clinic to Len Smith of Novo Nordisk® Pharmaceuticals, Inc., received Feb. 9, 2004.

(Continued)

*Primary Examiner*—Max F. Hindenburg
*Assistant Examiner*—Michael Astorino
(74) *Attorney, Agent, or Firm*—Len S. Smith; Reza Green; Richard Bork

(57) ABSTRACT

A method for providing a patient with an analysis result which the patient uses to determine a dosage of a drug for self-administration when the patient is unable to obtain the analysis result themself. The method involves gathering by the patient of information which affects the dosage, forwarding the information to an advisor who analyzes the information to obtain the analysis result, sending the analysis result to the patient, and determining by the patient of the dosage using the analysis result. The information can be gathered by the patient by using a digital camera to photograph an item of food, and the analysis result can be an amount of food. Preferably, the information and analysis result are exchanged via the Internet.

21 Claims, 30 Drawing Sheets

U.S. PATENT DOCUMENTS

| | | | |
|---|---|---|---|
| 6,018,713 A | | 1/2000 | Coli et al. |
| 6,024,699 A | * | 2/2000 | Surwit et al. ............... 600/300 |
| 6,076,166 A | | 6/2000 | Moshfeghi et al. |
| 6,085,752 A | | 7/2000 | Kehr et al. |
| 6,102,855 A | | 8/2000 | Kehr et al. ................. 600/300 |
| 6,139,495 A | | 10/2000 | De La Huerga ............ 600/300 |
| 6,151,581 A | | 11/2000 | Kraftson et al. ................ 705/3 |
| 6,161,095 A | | 12/2000 | Brown ........................... 705/2 |
| 6,168,563 B1 | | 1/2001 | Brown ........................ 600/301 |
| 6,478,736 B1 | * | 11/2002 | Mault .......................... 600/300 |
| 6,508,762 B1 | * | 1/2003 | Karnieli ...................... 600/300 |
| 6,513,532 B1 | * | 2/2003 | Mault et al. ................ 600/595 |
| 6,597,392 B1 | * | 7/2003 | Jenkins et al. .............. 600/301 |

OTHER PUBLICATIONS

Information concerning the American Diabetes Association 60$^{th}$ Scientific Sessions, San Antonio, Jun. 9–13, 2000 and other materials provided by Stroock, Stroock and Lavan.

Statement Concerning NovoTrack®/ MayoTrack Presentations, Diabetes Monitors and Diabetes Management Web Sites.

John D. Piette, BioMed Central, Abstract, Enhancing Support via Interactive Technologies.

Nebel et al., Patient Education and Counseling, vol. 46, Issue 1, pp. 55–59 (2002).

Nebel et al., Abstract, University of Leipzig, Germany.

Press Release, Area Malls Kick–Off Vismed Interactive Kiosks, www.touchvision.com/pr/marion.htm (2002).

Press Release, Novo Nordisk® Launches Interactive Diabetes Management Website www.findarticle.com (2001).

Gates et al., International Diabetes Monitor, vol. 15, No. 3, pages 1–6 (2003).

Smith et al., Diabetes Care, vol. 21, No. 6, pp. 972–976 (1998).

Montori et al., Diabetes Care, vol. 25, No. 11, pp. 1952–1957 (2002).

Diabetes In Control.com, Issue 117, item 2 (2002).

* cited by examiner

TRACK FAQS | Glossary | Credits | Legal | Home
① ② ③ ④ ⑤ ⑥ ⑦

GUIDE TO GOOD CARE

NOVO TRACK

Raff Ackermann
Personal Scorecard
Physician
Geoffrey Gates, MD
Diabetes Control
A1c 7.5 %
Next Appointment
04/20/01
NovoTrack Progress
37 of 35 topics
completed
Message Center - 0

DIABETES

Welcome to NovoTrack - your program to good diabetes care! This program was designed for you. You will find what you need to know about diabetes in the Guide to Good Care, Personal Scorecard and Message Center.

Guide to Good Care is a course in 7 tracks with 35 topics that were chosen to fit you and your diabetes. We recommend that you start at the beginning, but you can start anywhere and complete the topics in any order. Remember to answer the questions after reading each topic. You can reach the course by selecting a numbered button at the top of this page.

Personal Scorecard gives you access to vital information about your diabetes from your primary care provider. Explanations of each test help you to understand where you are now and where you should be going to reach the goals of good diabetes care. The Personal Scorecard can be reached from this homepage on the right or from the BioBox on the left of each page.

Message Center is a secure way to send messages to a nurse in your physicians office who can find answers to your questions about diabetes. The nurse will be following your progress through the Guide to Good Care. Remember that you and your physician make all the decisions about your individual medical care. Message Center can be reached from this homepage on the right or from the BioBox on the left of each page.

You can reach this homepage at any time by clicking on "NovaTrack" in the upper left corner or the "Home" menu item at the top of each page.

Now you are ready to get your diabetes on track - NovaTrack!

*PERSONAL SCORECARD*
Get instant access to vital info about your diabetes from your primary care provider. (GO)

*MESSAGE CENTER*
Post a message to a CDE who can answer your questions about diabetes. (GO)

FIG. 7B

NOVO TRACK

Raff Ackermann
Personal Scorecard
Physician
Geoffrey Gates, MD
Diabetes Control
A1c 7.5 %
Next Appointment
04/20/01
NovoTrack Progress
37 of 35 topics completed
Message Center - 0

DIABETES

FAQS | Glossary | Credits | Legal | Home
TRACK ① ② ③ ④ ⑤ ⑥ ⑦

TRACK 2: WHAT IS DIABETES?

Effects of Diabetes

A Healthy Life
People with diabetes can live long and active lives. Knowing how to treat your diabetes can help you avoid the symptoms of high and low blood glucose. Maintaining good diabetes control over time reduces the risk of long term complications.

No one would want to have diabetes, but those who rise to the challenge of good diabetes care may find strengths that they never knew they had.

High Blood Glucose
Both high and low blood glucose can cause symptoms that go away after the blood glucose returns to an acceptable level. In rare circumstances, extremes of either high or low blood glucose can lead to coma with results that may not be easy to reverse.

The symptoms of a very high blood glucose are thirst, excessive urination, fatigue, weakness and loss of weight. Other symptoms can occur including blurring of vision and difficulty healing wounds or fighting infections.

When your blood glucose is very high, the body can flush some of the excess blood glucose out of your system by putting it into the urine. You get thirsty as your body loses more and more water in the sugary urine. Frequent trips to the toilet can disturb sleep and interrupt activities during the day.

If a high blood glucose is left untreated, you can begin to lose weight. The weight you lose is not a healthy weight loss. Even though the blood glucose is high, the glucose can't get into the cells so the cells don't get the energy they need to do their work. Muscle is being broken down to make even more glucose. This results in weakness and fatigue.

At a certain level of blood glucose, the brain cannot function well. The most severe consequences of an extremely high bold glucose are confusion and eventually coma. These complications can be prevented by the most basic diabetes care.

Low Blood Glucose
Low blood glucose is usually the result of treatment that is not matched to a person's needs. This topic is covered extensively in Section 2 Using Medications Wisely.

Long-Term Complications
The complications of diabetes are not inevitable. High blood glucose can damage many different organs in your body. How diabetes damages an organ is complex and not completely understood even by scientists who study these problems. It has been shown by a number of studies that maintaining good control of blood glucose reduces the risk of complications. Control of other risks such as high blood pressure and cholesterol can also reduce the risk of complications.

People can live long and healthy lives with diabetes.

Thirst, excessive urination and other symptoms of diabetes do not occur until the blood glucose levels at extremely high.

Loss of vision (and other long term complications) can be prevented by good diabetes care.

Weight loss because of

FIG. 7D(1)

Each of the major complications of diabetes is discussed at greater length in Track 6 Complications.

Heart Disease
You may not think of a heart attack as a complication of diabetes – but it is! People with diabetes are at greater risk of diseases caused by cholesterol that builds up and blocks vital arteries. People without diabetes can get blockage in an artery leading to a heart attack, stroke or other circulatory complication. Diabetes just makes all of these complications worse.

Fortunately, various treatments have been shown to reduce the risk of heart disease and other circulatory problems for people with diabetes. You can learn more about this subject in Track 4 Treating High Blood Pressure and Treating High Cholesterol and in Track 6 Heart Disease.

Go To Questions high blood glucose is not healthy. A large part of the weight loss is muscle - with weakness and fatigue as a result.

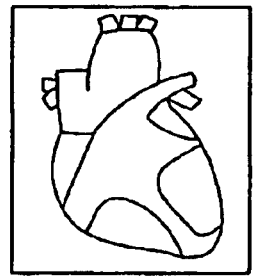

Diabetes increases the risk of heart disease. Good diabetes care reduces the risk.
SEE HOW
IT WORKS?

NOVO TRACK CDE CONSOLE

Profile | Message Center | Appointments | Outliers/Alerts

Back

Patient: Ralf Ackermann

| Table # | Topic | Date Completed | Minutes | Questions Correct |
|---|---|---|---|---|
| 5.4 | Asking for Help | 05/09/01 | 1 | 0 of 3 |
| 1.4b | Proof that Good Care Matters | 03/14/01 | 1 | 3 of 3 |
| 5.1b | A Healthy Attitude | 03/16/01 | 30 | 2 of 3 |
| 4.1b | How Diabetes Medication Work | 03/29/01 | 7 | 0 of 3 |
| 6.5b | Treating Heart Disease | 11/20/00 | 2 | 3 of 3 |
| 2.2b | What causes Diabetes | 03/29/01 | 20 | 3 of 3 |
| 6.7 | Dental Care | 05/09/01 | 2 | 0 of 3 |
| 4.4b | Hypoglycemia | 03/29/01 | 1 | 0 of 3 |
| 4.7 | Treating High Blood Pressure | 03/29/01 | 2 | 0 of 3 |
| 4.6 | Treating High Cholesterol | 05/17/01 | 23 | 3 of 3 |
| 6.1a | Preventing Retinopathy | 05/09/01 | 2 | 0 of 3 |
| 6.4b | Foot Care | 03/29/01 | 1 | 0 of 3 |

FIG. 7K

NOVO TRACK CDE CONSOLE

Profile | Message Center | Appointments | Outliers/Alerts

Patient: Ralf Ackermann

*Physician*

Date of last physician Appointment: [10/10/00]
Next Physician Appointment Goal: [4/20/01]
Actual Physician Appointment: [4/20/01]
*NOTE: Dates must be entered in the following format: m/d/yy or mm/dd/yr.*

*Ophthalmologist*

Date of last Ophthalmologist Appointment: [1/4/00]
NextOphthalmogist Appointment Goal: [1/4/01]
Actual Ophthalmologist Appointment: [10/25/01]
*NOTE: Dates must be entered in the following format: m/d/yy or mm/dd/yr.*

[ Save ]   [ Cancel ]

FIG. 7L

NovoTrack Guide To Good Care Outline

Key

| 0.0e | Title of the Topic | Medical Record Data | Patient Attitude Data | Questions |

Numbering sequence is by track, then topic. Note that a letter after the number indicates a choice of article for that topic depending on a patient characteristics entered by the patient in reponse to questions at the time of registration. Both the CDE and patient can edit data if required.

Track 1- Getting Good Care (4 articles: The section has 1 Medical Record choice and 1 Patient Attitude response at registration to choose perspective for the articles.)

| | | | | |
|---|---|---|---|---|
| 1.1 | Defining Quality Care | | | Questions |
| 1.2a | Caring for yourself | | New Diagnosis | Questions |
| 1.2b | Caring for yourself | | Established Patterns | Questions |
| 1.3 | Your Diabetes Care Team | | | Questions |
| 1.2a | Proof that Good Care Matters | Type 1 | | Questions |
| 1.4a | Proof that Good Care Matters | Type 2 | | Questions |

Track 2- What is Diabetes (4 articles: This section has 1 Medical Record choice at registration to choose perspective for the articles.)

| | | | | |
|---|---|---|---|---|
| 2.1 | Before You Had Diabetes | | | Questions |
| 2.2a | What Causes Diabetes | Type 1 | | Questions |
| 2.2b | What Causes Diabetes | Type 2 | | Questions |
| 2.3a | Effects of Diabetes | Type 1 | | Questions |
| 2.3b | Effects of Diabetes | Type 2 | | Questions |
| 2.4a | Who Gets Diabetes | Type 1 | | Questions |
| 2.4b | Who Gets Diabetes | Type 2 | | Questions |

Track 3 - Healthy Eating & Excercise (2 articles: This section has 2 Medical Record choice and 1 Patient Attitude response at registration to choose perspective for the articles.)

| | | | | |
|---|---|---|---|---|
| 3.1a | Healthy Eating | Type 1 | | Questions |
| 3.1b | Healthy Eating | Type 2 BMI<28 | | Questions |
| 3.1c | Healthy Eating | Type 2 BMI>28 | | Questions |
| 3.2a | Healthy Excercise | Type 1 | Sedentary | Questions |
| 3.2b | Healthy Excercise | Type 1 | Active | Questions |
| 3.2c | Healthy Excercise | Type 1 | Disabled | Questions |
| 3.2d | Healthy Excercise | Type 2 | Sedentary | Questions |
| 3.2e | Healthy Excercise | Type 2 | Active | Questions |
| 3.2f | Healthy Excercise | Type 2 | Disabled | Questions |

Track 4 - Using Medications Wisely (8 articles: This section has 1 Medical Record choice and 2 Patient Attitude response at registration to choose perspective for the articles.)

FIG. 8A

| 4.1a | Choosing The Right Insulin | Type 1 | | Questions |
|---|---|---|---|---|
| 4.1b | How Diabetes Medications Work | Type 2 | | Questions |
| 4.2a | Intensive Insulin Therapy | Type 1 | | Questions |
| 4.2b | Combinations of Medications | Type 2 | | Questions |
| 4.3a | Practical Tips For Insulin Use | Type 1 | | Questions |
| 4.3b | Insulin For Your Diabetes | Type 2 | Accepts Injections | Questions |
| 4.3c | Insulin For Your Diabetes | Type 2 | Rejects Injections | Questions |
| 4.4a | Hypoglycemia | Type 1 | | Questions |
| 4.4b | Hypoglycemia | Type 2 | | Questions |
| 4.5a | Monitoring Your Blood Sugar | Type 1 | Infrequent Monitoring | Questions |
| 4.5b | Monitoring Your Blood Sugar | Type 1 | Frequent Monitoring | Questions |
| 4.5c | Monitoring Your Blood Sugar | Type 2 | Infrequent Monitoring | Questions |
| 4.5d | Monitoring Your Blood Sugar | Type 2 | Frequent Monitoring | Questions |
| 4.6 | Treating High Cholesterol | | | Questions |
| 4.7 | Treating High Blood Pressure | | | Questions |
| 4.8 | Benifits of Asprin | | | Questions |

Track 5- Family, Friends & Feelings(4 articles: This section has 1 Patient Attitude response at registration to choose perspective for the articles.)

| 5.1a | A Healthy Attitude | | Optimistic | Questions |
|---|---|---|---|---|
| 5.1b | A Healthy Attitude | | Balanced | Questions |
| 5.1c | A Healthy Attitude | | Pessimistic | Questions |
| 5.2 | Setting Goals | | | Questions |
| 5.3 | Family & friends | | | Questions |
| 5.4 | Getting Help | | | Questions |

Track 6- Complications (7 articles: This section has 5 Medical Record choices and 1 Patient Attitude response at registration to choose perspective for the articles.)

| 6.1a | Preventing Retinopathy | Complication Absent | | Questions |
|---|---|---|---|---|
| 6.1b | Treating Retinopathy | Complication Present | | Questions |
| 6.2a | Preventing Newropathy | Complication Absent | | Questions |
| 6.2b | Treating Neuropathy | Complication Present | | Questions |
| 6.3a | Preventing Nephropathy | Complication Absent | | Questions |
| 6.3b | Treating Nephropathy | Complication Present | | Questions |
| 6.4a | Foot Care | Low Risk | | Questions |
| 6.4b | Foot Care | High Risk | | Questions |
| 6.5a | Preventing Heart Disease | No Ischemia | | Questions |
| 6.5b | Treating Heart Disease | Prior/Current Ischemia | | Questions |

FIG. 8B

| 6.6a | Smoking | | Nonsmoker | Questions |
|---|---|---|---|---|
| 6.6b | Smoking | | Smokes - Wants to quit | Questions |
| 6.6c | Smoking | | Smokes - Doesnt want to quit | Questions |
| 6.7 | Dental Care | | | Questions |

Track 7- Special Situations (5 articles: This section has 3 Medical Record choices at registration to choose perspective for the articles.)

| 7.1a | Driving | Type 1 | | Questions |
|---|---|---|---|---|
| 7.1b | Driving | Type 2 | | Questions |
| 7.2a | Traveling | Type 1 | | Questions |
| 7.2b | Traveling | Type 2 | | Questions |
| 7.3a | Employment | < 62 years old | | Questions |
| 7.3b | Retirement | > 62 years old | | Questions |
| 7.4a | Insurance | < 62 years old | | Questions |
| 7.4b | Medicare | > 62 years old | | Questions |
| 7.5a | Men's Sexuality | Male | | Questions |
| 7.5b | Women's Sexuality | Female, < 45 years Old | | Questions |
| 7.5c | Women's Sexuality | Female, > 45 years Old | | Questions |
| 7.6a | Sick Days | Type 1 | | Questions |
| 7.6b | Sick Days | Type 2 | | Questions |

FIG. 8C

ADAPTIVE INTERACTIVE PRECEPTORED TEACHING SYSTEM INCORPORATING REMOTE IMAGE MONITORING

CROSS-REFERENCE TO RELATED APPLICATION

This application is a continuation-in-part of copending U.S. patent application Ser. No. 09/877,492, filed on Jun. 8, 2001.

FIELD OF THE INVENTION

The present invention is directed generally to an adaptive and interactive system for teaching. More particularly, this invention concerns a system which tailors information sent to the student according to the student's identity. The system can provide for monitoring of the student's performance by the teacher and, where appropriate, direct communication between the student and teacher. Even more particularly, this invention involves a system which allows a patient to relay image data to the adaptive and interactive system for use in treating the patient and to obtain medical advice on the basis of the related image data.

BACKGROUND OF THE INVENTION

Knowledge can always be acquired by the truly inquisitive. However, certain formats are better adapted to specific goals.

An encyclopedia—whether in print, CD-ROM, or online—tries to encompass all knowledge that is relevant to a subject. The user of an encyclopedia expects to find the answer to virtually all questions about the subject. The most typical use of an encyclopedia starts with a query and ends with separating the relevant article, or even paragraph, from the mass of information that comprises the encyclopedia. Few users of an encyclopedia sit down to read the entire contents. In other words, an encyclopedia does not provide any cohesive educational framework which might guide the student.

Computer format encyclopedias have used various strategies to move beyond the limited role of answering queries. Feature articles that change each time the program is launched try to redirect the reader's attention to new subjects. Slideshows and guided tours also use the encyclopedias resources to draw the reader into areas where self-directed queries would never have gone. Encyclopedias can answer questions and even entertain the reader with knowledge, but none document the reader's competence in a subject.

A preceptored (taught) course is fundamentally different than an encyclopedia. The purpose of a preceptored course is to assure that a student who completes the course requirements has competence in the subject. A course may draw on the resources of an encyclopedia, but the lessons are arranged and directed by a teacher who sets objectives. The best teachers incorporate the interests of their students into the design of the course, but the overall direction of the course is still defined by standards that are set by experts to insure competence.

Live teaching has a number of drawbacks—the teacher must be compensated, space must be found for the program, and participants must all meet at the appointed place.

A further consideration is that live teaching draws upon limited resources. Patients being taught how to manage their diabetes may have only a single hour to speak with a dietician. If the patient is being taught how to estimate the nutritional value of a meal, the dietician may have to show the patient samples of food, say, rubber or plastic models, rather than the patient's own meal.

A further aspect of live teaching is that because of the limited availability of the teaching resources, the patient may have to wait longer than desirable to meet with their educator/healthcare provider. Patients might only meet with their educator/healthcare provider once every 3 months to review their blood glucose levels. This is a valuable time, during which the patient can be taught how to deal with particular or unique situations that are likely to arise, such as what happens when the patient goes to a late afternoon movie and consumes small snacks, followed by a very late dinner, or significant patterns, such as the patient showing higher blood glucose levels at bedtime whenever they eat in restaurants, instead of at home.

Physicians strive to provide the highest possible quality of care to those who have requested their services. Comprehensive education is an essential component of quality care for a person having diabetes. Physicians providing high-quality diabetes care may find their job complicated by the limited time that patients have available to complete their evaluations and the prohibitive costs of extensive individual instruction.

Thus, there is a substantial need for an educational program which provides the benefits of both encyclopedic and preceptored education.

One area where there is a pressing need for an improved educational system is in the ongoing treatment of diabetes. Good diabetes care challenges a person who often has no symptoms to make significant lifestyle changes and to take numerous medications on the belief that reaching certain numerical goals in the present will reduce the risk of complications in the future. Diabetes education has been recognized as an essential component of good diabetes care. Diabetes education should help patients acquire the knowledge and support the attitudes necessary to accept this challenge.

Improved outcomes have been demonstrated when the primary care provider combines an intensive program of patient education with attention to recommended quality of care measures. However, diabetes education is expensive and inconvenient to provide, while tracking quality of care measures can be lost in the details of providing care to a broad range of patients in a busy practice. Referring patients to community classes, suggesting books or even diabetes references online do not assure that the individual patient will acquire the knowledge and skills necessary to reach accepted quality of care measures.

An intensification of treatment is more likely to be successful if the change is made as soon as the patient is motivated to change. This requires that education to inform and motivate patients be linked directly to the physicians and nurses who have the ability to help patients make changes in their diabetes care.

A preceptored course with frequent testing and free communication between teacher and student assures that the student who completes the requirements has competence in the subject. Frequent communication with a knowledgeable health care provider can also sustain the motivation of a patient to adhere to the complex and burdensome requirements of good diabetes care. It is, however, expensive to provide such an education.

Neither computer games nor interactive educational programs for diabetes are new. However, no current program integrates a preceptored course of instruction with the tracking of individual quality of care measures from the patient's clinical record.

There is a further need for an interactive, adaptive educational system which can be used to improve diabetes care.

There is also a particular need for an interactive Internet educational course providing an alternative to individual counseling.

A further need exits for a system to increase the amount of time a diabetic patient receives individualized education from a healthcare provider.

A need also exists for a system which improves the ability of and time available for a healthcare provider to educate and monitor the status of a patient.

As part of the process of teaching patients how to manage their diabetes, patients are taught that the nutritional content of the food which they consume determines the amount of insulin which they require. One school of thought holds that carbohydrates should make up 50–60% of one's total caloric intake; proteins should make up 20–25%; and fats, from 20% to 30% (carbohydrates are broken down into glucose early during digestion and have the most immediate effect on blood glucose, meaning it is preferable to eat starches and other complex carbohydrates, rather than fruit juice and other simple sugars that have a rapid effect on blood glucose). Usually, doctors recommend three small meals and three to four snacks every day to maintain the proper balance between glucose and insulin in the blood. Overweight patients may be encouraged to lower their intake of fat and eat more complex carbohydrates and fiber.

An different school of thought favors the "Mediterranean" diet, in which the some of the carbohydrates are replaced with monosaturated fats such as olive oil. The present invention is equally applicable to the monitoring of such a diet, as well as any other type of diet.

Patients therefore learn that it is important for them to accurately determine the amount and nutritional value of foods that they consume so that they can calculate how much insulin to administer.

While patients may study how to estimate portion size and nutritional value with their diabetes care educator, it is unlikely that the diabetes care educator will be able to review with the patient every type of food that the patient might eat. Accordingly, patients usually only learn from their diabetes care educator the basics of estimating nutritional content, and it is likely the patient will from time to time be unable to properly judge the nutritional value of the foods they consume, for example, because the patient is not familiar with either the food or the food's manner of preparation.

Thus, there is also a need for a system which affords diabetes care educators more opportunities to help teach patients how to analyze the nutritional content of their meals, even in situations where the healthcare provider is not physically present with the patient.

Ulcers of the legs and feet occur in people with diabetes due to the combination of neuropathy and peripheral vascular disease. Neuropathy causes a loss of sensation, so that foot injuries may go untreated and become infected. Decreased circulation to the feet and legs slows healing. Proper nourishment does not reach damaged tissue, and infected material is not destroyed. If not properly cared for, even a small injury may progress to an ulcer, with serious consequences. Consequently, diabetics are encouraged to monitor their extremities, so that potentially troublesome wounds can be promptly spotted and treated. Patients may not, however, always be able to accurately determine whether a wound is medically serious.

Accordingly, there is also a need for a system which, when a diabetic patient discovers a wound on their body, allows the diabetic patient to have a medical professional study the wound to determine what type of care is appropriate.

SUMMARY OF THE INVENTION

In its preferred embodiment, the present invention links a patient's medical care in the physician's office to personalized education and brief online interactions with a nurse between office visits. This can improve the quality of patient care in a cost efficient manner.

The present invention is particularly suited for use with a preceptored diabetes course designed to help persons with diabetes obtain the best possible care. The course provides in a novel way reliable information on diabetes, and the information sent to patients is individually tailored based on each patient's registration data.

Providing tailored educational courses for patients has many benefits. Certain topics or perspectives will be appropriate for some patients but not for others. For example, a person with established diabetic retinopathy is more interested in options for treatment than in learning how they could have prevented this complication by better diabetes control. Other topics are based on the patient attitudes toward diabetes care that have been discovered in the patient's response to questions embedded in the program.

The technology of the internet can support an interactive education program customized to the patient and provide secure email communications with a preceptor. The present invention preferably employs the Internet to link the convenience of a personalized online diabetes course through secure communication with a nurse and/or the patient's physician. The physician can become involved when appointments are necessary.

A method for remote education of a student involves providing lessons, obtaining a profile for the student, the profile including at least one value describing one of the student's attributes, using the profile to select one of the lessons to be sent to the student, and sending the selected lesson to the student.

Another aspect of this invention relates to a method for the remote education of a student. This can be done by providing a set of lessons, obtaining a profile for the student which includes at least one value describing an attribute of the student, using the profile to select one of the lessons to be sent to the student, sending the selected lesson to the student, administering and then grading a quiz based on the selected lesson to the student, offering to inform the student of the quiz result, and offering to inform a preceptor of the time taken by the student studying the lesson and the quiz result.

If desired, the profile can be updated to reflect the quiz result. Information can be exchanged over the Internet, possibly in secure fashion. Student performance can be analyzed statistically.

Another benefit to this invention is that the educational process can be preceptored by a certified diabetes educator ("CDE"). The CDE monitors each patient in the course using website connection tracking data as well as the patient's responses to questions that are included with each course topic. Secure email allows the preceptor to offer encouragement as necessary. Patients can use secure email to ask the preceptor educational questions. Reports by the CDE/preceptor are sent to each patient and to each patient's physician. Patients "pass" the course by completing a required number of sections and achieving an adequate score on the factual questions in the text.

Each patient has secure access to their own healthcare data. This will provide the patient with a beneficial feeling of trust. Using a secure private webpage patients and their physicians can set goals and chart progress toward meeting these goals.

The present invention also can track performance of a group of patients, as well as individual patients in the group. Quality measures that could be monitored include patient satisfaction, knowledge, attitudes, behaviors and both clinical and laboratory based process outcomes. Reporting algorithms would accumulate data to satisfy the differing requirements of the several organizations concerned with diabetes care.

The present invention can be used to define clear objectives for the patients in the course. The objectives are chosen to improve clinical outcomes that have been shown to substantially affect the health of persons with diabetes. Educational content of the course may focus on changing behaviors that affect the attainment of these goals. Education of the person with diabetes is coupled with specific clinical and laboratory data that is shared with both the patient and the patient's physician. A CDE/preceptor monitors the patient's progress and sends prompts to the patients and their physicians as necessary.

Direct access to the educational content of the program is given to individuals. That way the program provides a modular lesson plan with computer tabulation and scoring of questions for registered users. The availability of a diabetes course can be supplemented by publicly available healthcare information such as that in comprehensive diabetes encyclopedias.

This invention is particularly concerned with a method for the remote care of a diabetic patient who is under the supervision of a healthcare provider. That method involves providing a set of lessons, obtaining a profile for the diabetic patient which includes a value describing one of the patient's attributes, using the profile to select a lesson to be sent to the patient, and sending the selected lesson to the patient for study. The system offers the patient information reflecting the patient's health, and also offers the healthcare provider information regarding at least one of the patient's study of the lesson, the patient's health, and the patient's medical appointments. The profile can reflect the patient's a1c or HbA1c level, urine albumin level, cholesterol profile, body weight, body mass index, blood pressure, foot sensitivity, upcoming medical appointment, or number of lessons that have been completed. Information can be exchanged using the Internet and in a secure manner.

It is also envisioned that the profile can be updated to reflect a change in the value. The healthcare provider can be alerted when the value crosses a predetermined level. The patient can be quizzed on the lesson sent, and the quiz results also can be used to update the profile.

A further aspect of this invention involves a remote education system for teaching patients how to estimate the size and nutritional content of their meals. Properly educated patients will then be able to determine the appropriate dose of insulin to administer to themselves. It is proposed that such remote education can be effected first by having the patient use a digital camera to take a photograph of their meal. The photograph is then sent to the healthcare provider, who can, by virtue of their greater experience, accurately determine the size and nutritional value of the meal. The healthcare provider then sends their nutritional estimate to the patient, possibly along with an explanation of how that estimate was obtained. Having this nutritional information, the patient can then administer the proper amount of insulin, and, equally important, can better learn how to estimate the size and nutrition of meals themself.

Among the ways in which this invention can be used is for the short-term education of diabetic patients while they are learning a meal planning system, such as carbohydrate counting or meal exchanges. Such educational schemes, which are themselves known in the art, may be more effective because patient interest may be increased through the use of digital imaging and Internet technology. Patient attitude toward the lessons may be improved because the patients receive a focused and personalized education for their condition.

Another situation where this invention may be of particular use is to help patients starting on an insulin pump or intensive insulin therapy. In that situation the patient could send meal images, along with blood glucose data, to an expert diabetes educator or physician so that adjustments in the patient's insulin dosage could be made, either in real time or at periodic intervals.

The transfer of data between the patient and the healthcare provider can be effected using the educational system already described. For instance, in the foregoing situation, a record of the insulin dose decisions made could be kept in the interactive preceptored education system, in order to facilitate the improved fitting of insulin dosing to insulin requirements based upon comprehensive information, such as blood glucose data and meal content.

If desired, it may be possible to use a computer program to estimate the nutritional content of the patient's meal.

Still another aspect of this invention concerns a system which allows a diabetic patient who discovers a wound to take a digital photograph of the wound and have the wound evaluated on the basis of the photograph. Such evaluation could be performed by a healthcare provider or computer program. This approach need not be limited to diabetics—anyone with a wound or other ailment requiring visual monitoring could use such a system.

Other features and advantages of this invention will become apparent in the following detailed description of preferred embodiments of this invention, taken with reference to the accompanying drawings.

BRIEF DESCRIPTION OF THE DRAWINGS

FIGS. 8A–C depict a content matrix containing educational modules which are used in the present invention;

DESCRIPTION OF THE PREFERRED EMBODIMENT

Figure 1:
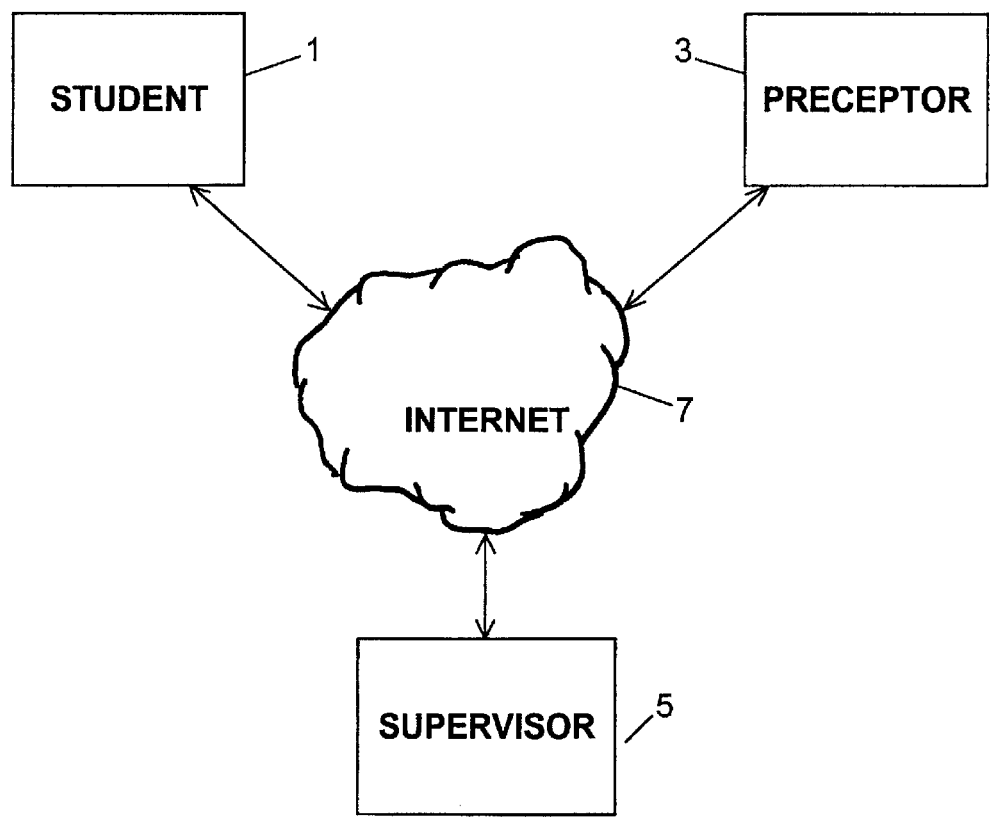
FIG. 1 depicts a scheme for an adaptive interactive preceptored teaching system for communication using the Internet between a supervisor, a preceptor and a student.

The present invention relates to a system for remote learning in which at least some of the educational content sent to the student is selected based upon one or more identifying characteristics of the student. In other words, this invention adapts the educational program to take into account the identity of the student. Although educational content is delivered automatically, the system is preceptored in that the system keeps track of each student's performance. Where a student's performance falls below some predetermined minimum level, the system alerts the preceptor, who can take suitable action such as making direct personal contact to help the student learn.

The following definitions are used in the description of this invention:

CDE: certified diabetes educator, a nurse or other health professional having specialized training in the care and monitoring of diabetics.

Content Matrix: refers to a collection of educational modules which are selected and sent to students. Different students may receive different modules so as to tailor teaching content to the students' own needs.

Educational Content: the collection of educational modules from the content matrix which are sent to a student.

Educational Module: a single entry in the content matrix having information to be taught to the student and which also may include questions to measure the student's proficiency with the material studied.

Healthcare provider: a physician, nurse, certified diabetes educator or other health professional.

Patient: person under the care of a physician and a CDE. The patient is a student.

Physician: doctor having supervisory responsibility for a patient.

Preceptor: person having direct responsibility for educating a student by monitoring the student's performance and, when appropriate, intervening to provide the student with additional teaching. That additional teaching can involve using the adaptive system to provide the student with opportunities to repeat lessons already studied or to cover new lessons. If appropriate, the preceptor can provide the student with direct teaching, whether by remote communication such as e-mail or in person. A CDE is a preceptor.

Profile: A set of criteria such as gender or age corresponding on an individual basis to member of a group of students, and which determines the educational content that is sent to the member.

Quiz: any interactive scheme for determining a student's mastery of an educational module. Commonly given in the form of a series of multiple choice questions.

Student: an individual participating in an adaptive interactive preceptored teaching system.

Supervisor: an individual such as physician having oversight responsibility for the interactive preceptored teaching system.

This invention generally involves a remote automated tailored teaching system through which a student, preceptor and supervisor all can interact via communication lines and the Internet. The student is sent educational content chosen to fit the student's particular needs, and the student, preceptor and supervisor can monitor the student's performance. Should the student's performance become unacceptable, the system will notify the preceptor and/or supervisor so that remedial action can be taken.

The present teaching system is intended to improve the educational process by increasing a student's interest in learning. Students often learn best where they receive personalized education, and where the material taught has direct applicability for the students. To help maintain the student's enthusiasm, the teaching system sends each student status information showing how the student has performed in the past. To personalize the education process, the system employs a profile of relevant student information to determine what educational information should be sent. By way of non-limiting example, each student could be sent performance data summarizing their results on previous quizzes. Students also could be sent information comparing their performance to that of others using the same teaching system, i.e., each student could be told their current rank in the group.

The term "group" is used loosely, and refers to a collection of students who are engaged in the same course of study. The students need not be in each others presence, nor need the students even know of the existence of other members of the group.

More specifically, the present invention can for any student call up that student's profile information. Using suitable decisionmaking algorithms to select appropriate education modules the system generates and sends to the student educational content tailored to the student's own profile.

While one focus of this teaching system is to provide an automated remote teaching system, another is to automatically alert the preceptor to any student whose performance is becoming unsatisfactory. This way, the preceptor can offer a student having difficulty additional instruction. By way of non-limiting example, additional instruction could involve repeating all or part of a previous program of educational content, or could consist of direct one to one instruction by the preceptor.

Other aspects of this invention allow preceptors and the supervisor to statistically analyze the students' test results. Statistical analysis can serve a two-fold purpose. Analysis can help to identify students having particular difficulty with the educational program, and it also can be used to determine whether any portions of the teaching materials and/or their corresponding quizzes may require modification. That is, portions of the educational program having significantly lower pass rates than other sections may not be sufficiently clear, and so may benefit from rewriting. Preceptor performance also can be monitored in this manner.

Another way to look at the present invention is as a system for facilitating communication between the supervisor, preceptor and student. With reference now to FIG. 1, it will be seen that student 1, preceptor 3 and supervisor 5 all exchange information via the Internet 7 (the Internet and the manner in which communication over the Internet is performed are discussed elsewhere in this disclosure). Each party can both send and receive data over the Internet.

In some cases it may be appropriate to provide for secure communications between each of the parties. In that case, known security protocols can be employed. By way of non-limiting example, each supervisor 5, preceptor 3 and student 1 can be given a unique login name and password which must be accepted by the system before the system can be accessed. Although FIG. 1 depicts only one supervisor 5, preceptor 3 and student 1, it should be understood that this is also by way of example and not limitation.

Communication is an important part of the education process. The present system enables the student 1 to communicate electronically both with the preceptor 3 and the supervisor 5. By way of non-limiting example, the student 1 can send and receive e-mail messages with both the preceptor 3 and the supervisor 5. The student 1 also can both electronically check his previous performance and receive new educational content. Education content can be tailored to the student's own needs. If the education program includes a testing component, the student 1 can send his test answers in using the Internet. Test results can be returned to the student 1 by Internet as well. Where the student's performance may fall below some acceptable minimum, the student 1 can be sent a warning and additional educational materials. The student 1 even may even be able to engage in independent study, say, by looking at a list of Frequently Asked Questions ("FAQ"), or studying content modules of personal interest contained in a general searchable matrix of modules. Links to other sources of relevant information such as government websites also could be provided.

With continued reference to FIG. 1, supervisor 5 generally serves an oversight function, making sure that the educational program as a whole is operating effectively. To accomplish this goal, supervisor 5 can monitor certain indicators which reflect the performance of each student 1 and preceptor 3. Another aspect of this invention therefore involves providing the supervisor with a data analysis package for statistically evaluating test results. Using the data analysis package the supervisor 5 can measure student and preceptor performance and also can see whether any of the educational materials require modification.

To this end, the supervisor 5 can communicate individually and securely with each preceptor 3 and/or patient 1.

Preceptor 3 plays several roles in this teaching system. Preceptor 3 is responsible for registering new students 1 so that they can use the teaching system, responding to all questions that students 1 may pose, and serving as a bridge between the students 1 and the supervisor 5. Preceptor 3 also monitors the performance of each student 1 to verify that the student 1 is mastering the material being taught. This monitoring might involve checking each student's quiz scores to identify those students having difficulty learning the material presented. Alternatively, a more complex statistical analysis could be conducted.

When student 1 has been identified as not performing at the required level, the preceptor 3 can contact that student 1 and arrange for remedial action such as having the student 1 repeat one or more lessons or receive intensive one-on-one tutoring with the preceptor.

Preceptor 3 can communicate with supervisor 5 to seek advice for an student 1 whose performance indicates the student 1 may require special attention. Preceptor 3 also can communicate with supervisor 5 if a student 1 asks a question which the preceptor 3 is unable to answer, or where preceptor 3 herself has some question. The preceptor 3 also can respond to questions posed by supervisor 5.

Figure 2:
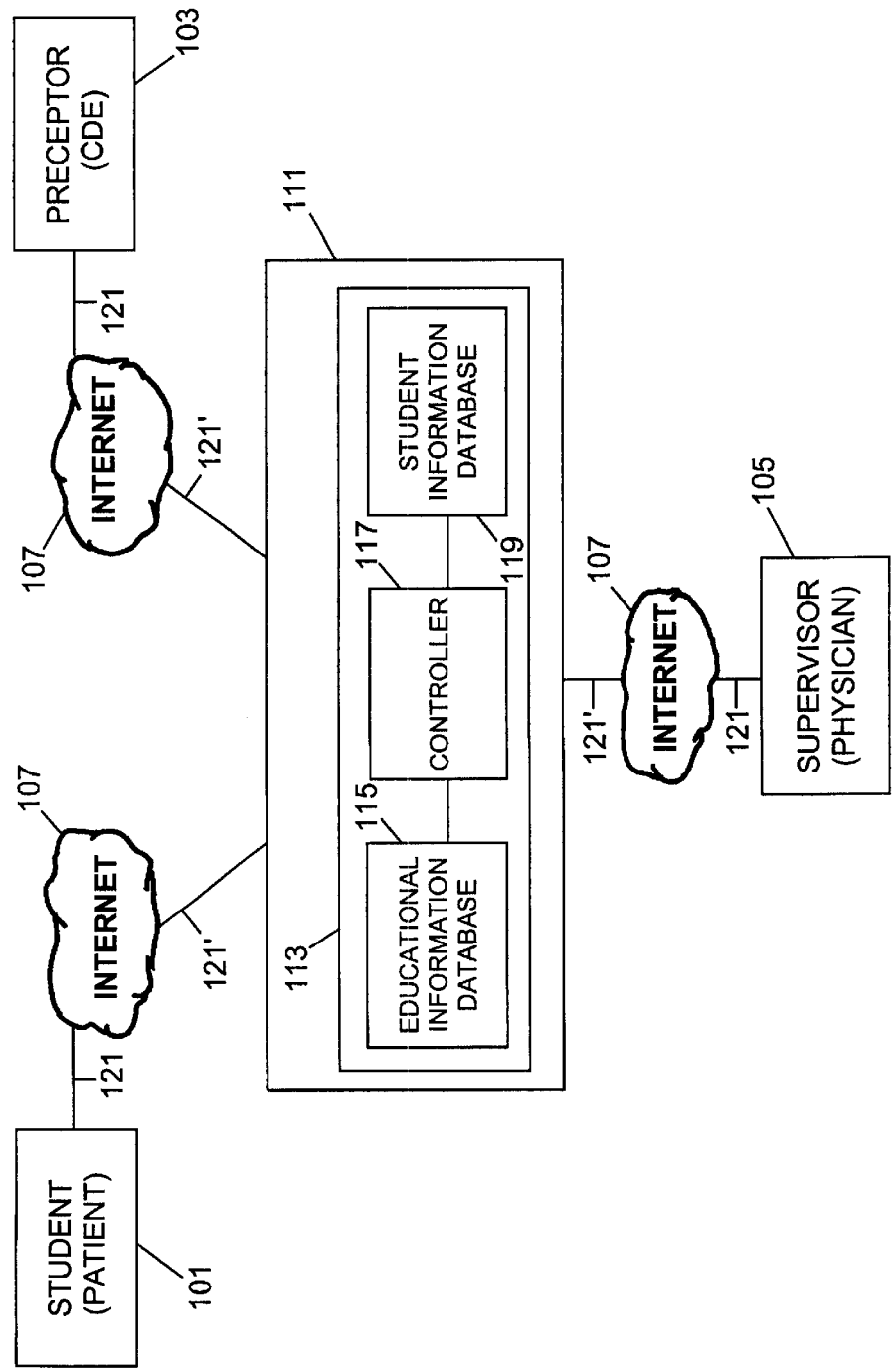
FIG. 2 is a schematic view showing components of the system depicted in FIG. 1.

Turning now to FIG. 2, a preferred embodiment of this invention will be discussed.

As FIG. 2 shows, student 101, preceptor 103 and supervisor 105 interact with one another through a teaching system 111. By way of non-limiting example, communication can take place at least in part using the Internet 107. Student 101, preceptor 103 and supervisor 105 each communicate with the Internet 107 via signal lines 121, and teaching system 111 communicates with the Internet '107 through lines 121'. It should be understood that although FIG. 2 depicts three Internets 107, they are the same Internet 107. Lines 121' could all be the same line or could be separate lines.

The student 101, preceptor 103 and supervisor 105 can access the Internet in known manner, for instance, by using personal computers (not shown).

By way of non-limiting example, teaching system 111 can include a computer server 113 of known design. Computer server 113 functions to route information such as messages between student 101, preceptor 103 and supervisor 105, and performs other functions which will be described.

As depicted in FIG. 2, computer server 113 includes an educational information database 115 and a student information database 119. Controller 117 has access to the information in databases 115 and 119, and can retrieve data from and write data to each of those databases 115 and 119.

Educational information database 115 contains a number of distinct education modules (not shown). Each module can correspond to a single lecture, education program or article. Modules can be constructed which may be of interest to a particular subset of the group being educated. Subsets of the group can be based upon characteristics such as gender, age, occupation, medical condition and so forth. For instance, a module could be written in a manner tailored to reflect the interests of a young person, and a corresponding module could be written in a way reflecting the interests of an older person.

Student information database 119 stores profile information (not shown) for each student. Such profile information can include, but need not be limited to, information which can be used by the controller 117 to determine which educational modules from the educational information database 115 are to be forwarded to student 101. By way of illustration only, in the foregoing example the student information database 119 may include age information for each student in the group. This way, when the controller receives a request from student 101 for educational information, the controller 117 would access the profile for that student 101 in the student information database and obtain the student's age. The controller 117 would then select from the educational information database 115 the educational module which is appropriate for the student's age.

Profile information may in part be based upon the student's answers to registration questions. The student can answer those questions as part of the initial registration procedure for using the teaching system. Provisions can be made for changing the student's answers.

Each of the educational modules sent to student 101 via the Internet 107 and lines 121, 121' preferably includes a quiz having one or more questions intended to measure the student's mastery of the material taught. The student 101, after receiving and completing the quiz, returns the quiz to the teaching system via the Internet 107 and lines 121, 121' for grading.

Controller 117 then looks to educational information database 115 to obtain the answer key for the quiz and grades the student's answers accordingly. The quiz results can be communicated to the student in several ways. By way of non-limiting example, the controller 117 automatically sends the quiz results to the student 101 as a message. Alternatively, student 101 may send the teaching system 111 a request for the quiz results, and in response the controller 117 sends those results to the student.

The graded quiz results can be sent to the student 101 either individually or in groups. For instance, the grades for all of the modules on a particular subject could be sent to the student 101 at the same time.

Another function performed by the teaching system involves the statistical analysis of both student 101 and preceptor 103 performance. By statistically analyzing student performance to identify any student 101 whose performance is substantially below that of others in the group, the preceptor 103 can be alerted to take appropriate remedial action to aid the student 101. Promptly taking remedial action means the student 101 should not fall far behind other group members.

Statistical analysis also can be used to determine the preceptor's effectiveness. Preceptor performance can be measured by comparing the performance of one preceptor's group of students to the performance of the other preceptors' groups of students, or to a historical reference database or standard.

Statistical analysis of student performance also means that test material effectiveness can be evaluated. Questions, whether multiple-choice or fill-in, found to have statistically aberrant pass rates may be too difficult or too easy. For example, where a question has a much lower pass rate for all students than other questions in the quiz, it is likely that the question is confusing or tests material that the students have not mastered. In like manner, a question found to have a much higher than expected pass rate may be too easy.

Once identified, questions having unexpected pass or failure rates can be reviewed and, if necessary, reworked or deleted.

The statistical methods which are used to analyze student and preceptor performance and question effectiveness are themselves known, and so will not be described further.

Controller 117 also performs functions such as routing messages between student 101, preceptor 103 and supervisor 105. Byway of non-limiting example, messages may take the form of e-mail communications. Known e-mail schemes can be employed.

Depending upon the nature of the educational program implemented it may be desirable to insure that the teaching system is secure against unauthorized use. The teaching system can therefore require students, preceptors and supervisors to log in using a recognized login name and password. Until a recognized login and associated password are entered, the system will not allow further action. This will prevent unauthorized tampering with the system.

The creation, maintenance and deletion of login names and passwords is typically performed by a system administrator. In the present invention it is envisioned that the preceptor will be able to create student-level logins.

Depending upon the subject matter being taught and the nature of the information being sent, for example, student personal data, secure communications between each of the students 101, preceptor 103 and supervisor 105 and the teaching system 111 may be required. Such secure communication can be carried out in known fashion using available secure e-mail and Internet-based communication systems.

A particularly preferred embodiment of this invention for use in the treatment of diabetes will now be described.

Diabetes is a widespread and serious illness affecting millions of people worldwide. Proper diabetes care requires constant monitoring and action by both those affected and their healthcare providers. Typically, diabetics monitor on a regular basis basic vital signs such as blood glucose and cholesterol. Diabetic care also includes an educational component; patients receive instruction in the causes, symptoms and treatment of diabetes, and are taught by Certified Diabetes Educators (CDEs) how to properly care for themselves. They also must regularly visit their physicians to have their general health assessed. Physicians study various indicators to evaluate a patient's condition. Blood chemistry, foot sensitivity, eyesight and blood circulation all may be checked.

Because such monitoring, care and education is time consuming, patients may gradually "slack off" and become less vigilant in their efforts. Consequently, anything which can be done to maintain patient interest in their own care so that they continue to monitor properly their condition, meet regularly with their CDE and physician, and continue their education can improve patient health.

The present invention is well-suited for diabetic care. Because this invention tailors the educational process to reflect the needs of each patient (student) and provides each patient (student) with an assessment of their performance, those using this system receive personalized health care. Diabetics, like most people, enjoy receiving attention; where patients are able to participate in a health care program which they perceive as being tailored to their own needs they may be more enthusiastic about the program and more likely to adhere to the program's guidelines.

Patients also may like the convenience of a remote education and monitoring system, since they can study at home. Patients also may enjoy the "high-tech" aspect of this system, which allows them use a personal computer to study, monitor their health and communicate with CDEs and physicians using the Internet and e-mail.

In the following discussion of particular aspects of this embodiment, the terms "patient", "CDE" and "physician" are respectively synonymous with and are used in place of "student", "preceptor" and "supervisor".

Next the manner in which the physician, patients and CDE' interact with the teaching system will be discussed.

Physician Use of System

Figure 3:
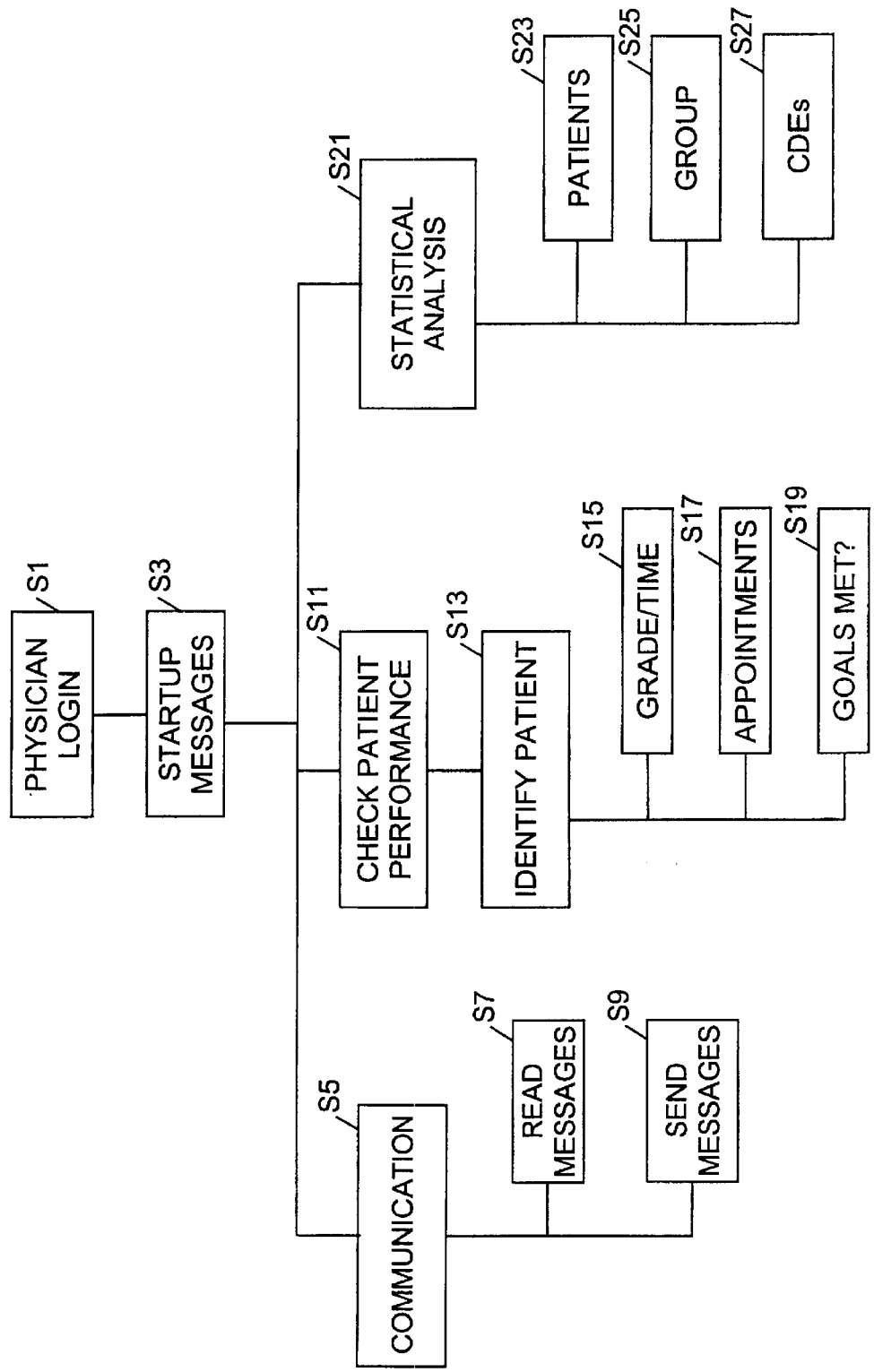
FIG. 3 is a flowchart illustrating various actions which can be taken as the physician (supervisor) uses the system depicted in FIGS. 1 and 2.

As depicted in FIG. 3, the present invention allows a physician to monitor the performance of each participating diabetic patient under the physician's care. The physician also can monitor the CDE's performance. If necessary the physician can communicate with patients and CDEs via secure e-mail. This functionality is provided through the use of suitable server software at the website on which the teaching system is hosted and client software loaded on the physician's own personal computer.

The physician accesses the teaching system by submitting a login name and password in step S1. The teaching system then returns a message either confirming or denying access, the latter being sent where incorrect or expired login information has been used.

Once the physician has accessed and been accepted by the teaching system the system in step S3 sends the physician startup status information. Preferably, the system first notifies the physician of any urgent matters. By way of non-limiting example the system may notify the physician of any patient who has requested immediate contact with the physician or who has otherwise indicated a pressing medical problem. Urgent messages from the CDE also can be displayed.

This urgent information can be displayed by itself on a webpage or it can be displayed as part of another webpage. It is thought that the importance of this information will be best appreciated if the information is displayed by itself.

After notification of any urgent matters the system can then display general status information for the entire group of patients, such as the group's average test score, general level of compliance with the diabetes care program, and so forth. This will give the physician enough information to determine whether immediate action is required. For instance, special situations can be brought to the physician's attention. By way of non-limiting example, patients missing more than a predetermined number of doctors' appointments over a particular period of time may be identified. Other indications of poor patient compliance with the care program, such as a patient's receiving a very low score on a quiz, may be listed.

As with the urgent information, the non-critical information can be displayed by itself or it can be included in a box on a webpage containing other information as well.

A calendar of upcoming appointments with patients or other events also can be included, either as its own webpage or as part of another webpage.

Following display of any urgent information and any opening messages, the system displays a main webpage from which the physician can access all of the available system functions. These functions can include the following: communications; individual performance status; and statistical analysis.

As shown in step S5, the physician, using the system's communication function, can both read messages received from others in step S7 and send messages to others in step S9. These functions can be implemented in whole or in part using an available e-mail program such as Microsoft Outlook, Microsoft Outlook Express, or Lotus ccMail.

The physician also can in step S11 check on an individual patient's status to see how the patient is interacting with the teaching system. After activating this portion of the system in step S11, the physician in step S13 identifies the patient for whom information is sought. This can be done by entering the patient name or selecting the patient's name from a displayed list of group members.

Having selected the patient for whom information is sought, the physician can choose to receive any of several different categories of information. In step S15 the physician can check to see how the patient's education is proceeding. By way of non-limiting example, the physician receives the patient's quiz grades, sees how long the patient spent on the quiz, as well as how long it took the patient to complete the lesson corresponding to the quiz.

In step S17 the physician can see whether the patient has been keeping his appointments with healthcare professionals, including the CDE and any other doctors. This can be informative because a sudden change in attendance habits or absenteeism may be an indication that the patient is having problems.

As explained in greater detail below, the present invention provides each patient with a set of goals, such as attaining a particular body weight, changing their blood glucose readings to a certain value, and completing a set number of educational lessons on the subject of diabetes. The physician can in step S19 monitor the patient's efforts to achieve these goals, and, if necessary, take suitable action such as giving the CDE instructions or contacting the patient with congratulations or to discuss the patient's efforts. It is envisioned that when the physician requests this information the system displays that information in tabular form, which can aid the physician in evaluating the patient's performance. By way of non-limiting example, goal information could be displayed in column format, with the first column identifying the nature and numerical value of the goal (i.e., body weight 145 lbs), the second column reflecting the patient's level of performance (i.e., weight 147), and the third column numerically quantifying the patient's performance (i.e., weight 101.9% of goal). Taken together this information may help the physician to evaluate the patient's efforts.

Alternatively, all of the foregoing information could be displayed immediately on a single web page once the physician has identified the patient for whom information is sought.

As shown in FIG. 3, the physician can also obtain a statistical analysis S21 for patients, groups, and CDEs. Statistical analysis can be a powerful tool for detecting when a patient may not be following a proper course of care. In step S21, the physician can request statistical information for the patient, group of patients or the CDE in steps S23, S25 and S27, respectively. Using statistics it is possible to determine when poor patient performance is more than an isolated occurrence, but rather, is indicative of a more serious problem. Statistics also can be used to determine when all members of the group are reacting in the same way, as might be the case where a question in one of the quizzes testing mastery of an education module is ambiguous.

Statistical analysis can be a powerful tool for detecting when a patient may not be following a proper course of care. The physician can request statistical information for the patient, group of patients or the CDE in steps S23, S25 and S27, respectively. Using statistics it is possible to determine when poor patient performance is more than an isolated occurrence, but rather, is indicative of a more serious problem. Statistics also can be used to determine when all members of the group are reacting in the same way, as might be the case where a question in one of the quizzes testing mastery of an education module is ambiguous.

In the same way statistics can be used to see whether the CDE's performance deviates significantly from that for other CDEs. For instance, if it is found that the number of patients of a particular CDE who routinely miss medical appointments is statistically greater for one CDE than for other CDEs, it is possible that the CDE is not emphasizing sufficiently the importance of keeping such appointments. In that case the physician can contact the CDE to discuss this point and suggest ways to improve the CDE's performance.

Patient Use of System

Figure 4:
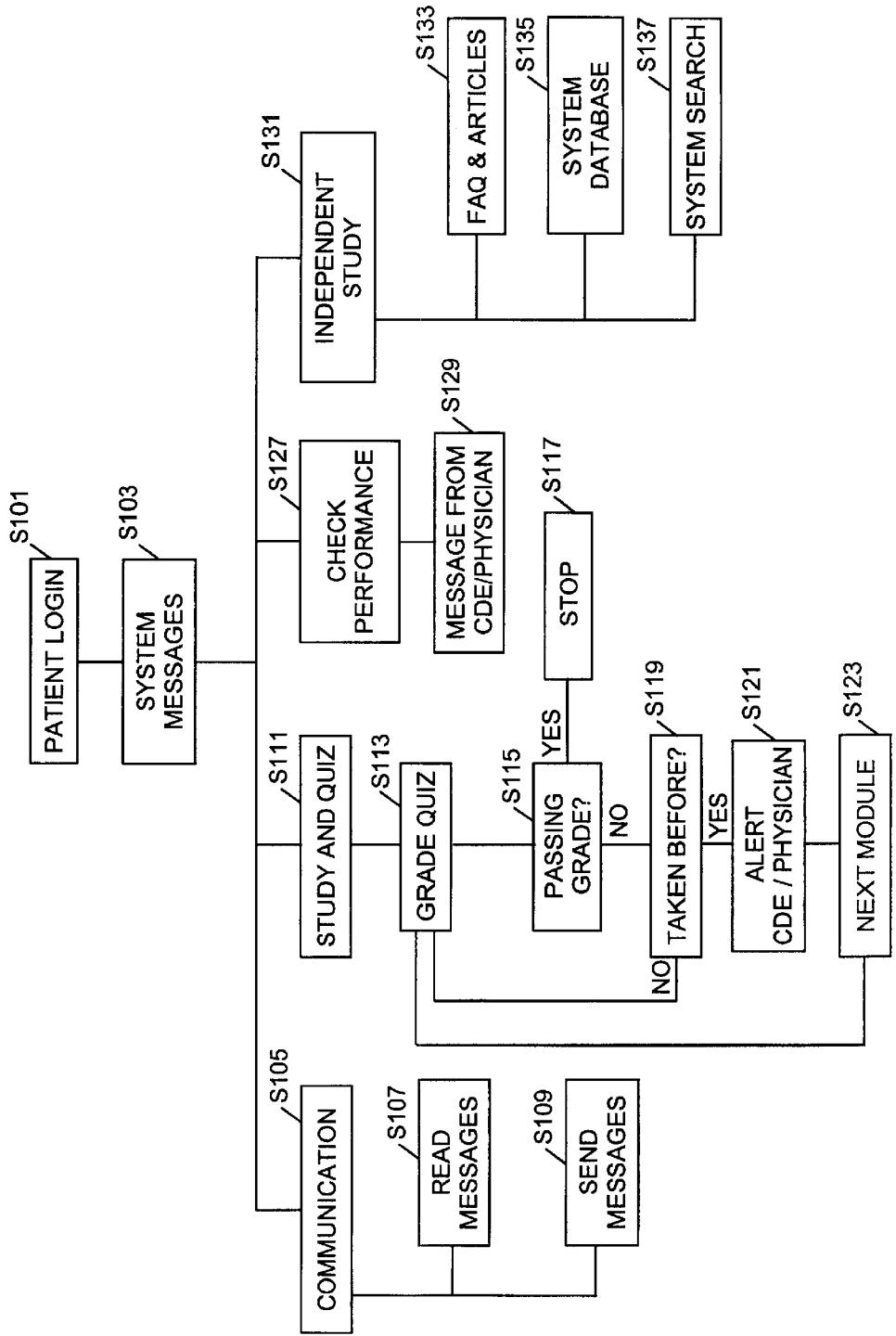
FIG. 4 is a flowchart illustrating various actions which can be taken as the patient (student) uses the system depicted in FIGS. 1 and 2.

Use of the teaching system by a patient will now be explained in connection with FIG. 4.

As previously noted, patient participation may be improved when patient interest in the program is increased. To this end, the webpages sent to the patients should be interesting enough to attract and retain patients. To emphasize that the teaching system is personalized, it may be beneficial to put each patient's picture and the picture of their physician on "their" webpages.

To insure privacy and security, the patient first submits a unique login name and password in step S101. Only after the login name and password have been accepted can the patient obtain access to the teaching system. The patient cannot access information for other patients.

The teaching system then returns a message either confirming or denying access, the latter being sent where incorrect or expired login information has been used.

When logged into the system successfully the patient receives in step S103 one ore more welcome messages and any other messages that might be appropriate for immediate viewing. By way of non-limiting example, the system could inform the patient of important upcoming events such as medical appointments. Urgent messages from the patient's physician or CDE also could be displayed (as discussed below, messages of less importance could be selectively retrieved by the patient using the system's e-mail function).

As with the physician portion of this system, the urgent information can be displayed by itself on a webpage or it can be displayed as part of another webpage. Again, the importance of this information may be best recognized if the information is displayed by itself.

After notification of any urgent matters the system then displays a home webpage from which the patient can access all of the available system functions. With continued reference to FIG. 4, exemplary system functions include e-mail access, study of diabetes educational materials, monitoring of the patient's personal goals and independent study and/or search of a general diabetes encyclopedia/database. Each of these functions will now be discussed in turn.

As shown in steps S105 the patient can access the portion of the teaching system allowing for the exchange of e-mail. Using the systems communication functions, the patient can in steps S107 and S109, respectively, retrieve and send e-mail messages. Messages can be exchanged with the CDE and physician. Optionally, a patient also could exchange messages directly with other patients, or post messages on electronic bulletin boards. The patient, like the physician, can use an available program such as Microsoft Outlook, Microsoft Outlook Express, or Lotus ccMail to handle e-mail.

As already noted, education is an important part of diabetes care. Patients who are kept informed of the latest developments in diabetes treatment can take better care of themselves. The teaching system provides in step S111 for a remote study program in which a patient can access customized study materials using the Internet. After studying those materials the patient is quizzed to evaluate whether they have mastered the subject matter.

One particular benefit of this invention is the educational materials sent to each patient are selected according to the patient's needs. This way each patient receives an education tailored to their medical state. This manner of education is highly efficient; patients only learn what they need to know. By way of example, men need not be educated in areas of concern only to women. Younger people need not be taught about subjects which are only of concern to the elderly. People who are underweight need not be educated about how the obese should treat their diabetes. Moreover, patients may perform better and be more enthusiastic when told they are being taught just what is important for their particular medical condition.

Another important component of this invention is the content matrix, this being the name for the entire collection of all educational modules. The content matrix should be carefully prepared with educational modules for all patients, regardless of their individual profiles. In the case of diabetes it is envisioned that the content matrix defines a course having 35 topics (modules) arranged in 7 "tracks". To insure easy readability, each topic can be from about 500–900 words long, and to help generate interest may include graphics and interactive questions. In the case of diabetes case it is preferable that the course should cover the topics recommended by the American Diabetes Association for a comprehensive education in diabetes care.

The 35 topics can be chosen from a database of articles or can be prepared specifically for the teaching system. The selections sent to the patient are chosen according to data from the patient's medical record and their responses to a questionnaire on attitudes and behaviors. By way of non-limiting example, modules should be available which are appropriate for any age patient, those with and without cholesterol issues, long-term and newly-diagnosed diabetes, and so forth. Some modules may be applicable to all patients, regardless of their profile. Other modules may only be relevant for a small group of patients. Articles forming the course will therefore be specific to the patient's type of diabetes and health status as well as their attitudes and behaviors. There are about a quarter million unique combinations of articles, making this a truly customized education procedure.

The manner in which this scheme is implemented will be discussed elsewhere.

Rather than have patients complete successive educational modules, it is preferable for each patient to finish a module and then take a short quiz keyed to the contents of that module, as shown in step S111. People who know they will be tested on a subject often study with greater diligence. A further benefit to testing a patient on each educational module is that it will be possible to identify promptly patients who are not retaining the information that has been taught.

Preferably, the quiz given in step S111 is multiple choice; this way, the patient's answers can be graded automatically. Other question forms such as filling in the blanks or drop-down menus can be used, and it even may be possible to employ artificial intelligence and handwriting analysis to automate grading of such quizzes.

To maintain patient interest, quiz formats may be varied. Some educational modules could have 1–2 simple questions, followed by text and graphics (even animations) to cover the topic, and then finish with 2–3 more questions. Educational modules can deviate from this pattern as appropriate. For example, a section called "What's Your Diabetes Attitude?" could be mostly a questionnaire with an explanation of the results. This section would be built around a validated research tool such as the DAS 3 (Diabetes Attitude Survey). Another example could be "How's Your Vocabulary?", which could have a crossword puzzle on diabetes linked to a glossary.

The grade for the quiz automatically generated and returned to the patient in step S113. The system checks in step S115 whether the patient's grade is greater than a predetermined minimum passing grade. If so, no further action is taken or a congratulations message on behalf of the CDE or physician could be sent in step S117. Should, however, the patient have failed the quiz, the system can instead send the CDE and/or physician an alert.

Optionally, the system can check as in step S119 whether the patient has taken the quiz before. If the patient has not take the quiz already, processing returns to step S111, where the patient is given an opportunity to study the educational module again and thereafter retake the quiz. If after retaking the quiz the patient is found in step S115 to have passed, no further action is taken or a congratulatory message can be sent. If, however, the patient has again failed in step S115 the system can send the appropriate alert to the CDE and/or physician in step S121. In addition, the system may in step S123 invite the patient to study a different educational module. This way if the patient passes the new educational module's quiz they will complete the session with a positive feeling of accomplishment, despite failing the previous educational module. The patient is not invited to study the failed educational module a third time, since the likelihood of a patient passing a quiz on the third try is remote, and meaning it may be more efficient to have the patient move on to another section. Instead, the CDE and/or physician, having been notified in step S121 that the patient has twice failed a module, can take personal action to teach the patient.

Insofar as the foregoing discussion speaks of sending an alert to the CDE and/or physician, it should be understood that such an alert could be an e-mail message. The CDE and/or physician could receive a "pop-up" message or could retrieve that e-mail message at their convenience.

The patient also can use the teaching system as in step S127 to monitor their own performance on quizzes. After checking their performance in step S127 the patient may receive a message from the CDE or physician in step S129, possibly commenting on their performance or giving them other advice.

In addition, the patient in step S127 could check to see if they are being successful in caring for themselves and are succeeding in attaining their medical goals. For instance, a patient could check her "personal scorecard" to see whether her cholesterol has decreased to a goal level. The personal scorecard includes a page with the patient's demographic and clinical information that the patient can check for accuracy. Interim (such as by the next appointment) and/or personal goals are set and recorded for each patient based on consultation with the physician. An explanation of each value and/or goal can be provided, either as a text explanation or as a link to an article covering the subject. The personal goals may differ from the optimal goals if there are mitigating circumstances (e.g. hypoglycemic unawareness). This scorecard helps patients chart progress toward achieving behavioral commitments (e.g., checking feet daily, exercising so many minutes per weekday or substituting a low fat for a more typical high fat choice in so many meals per week).

By way of example, self-monitoring of blood glucose records could be plotted and analyzed with software developed for the DMR, Your Diabetes World or other diabetes monitoring programs and be used to update the appropriate personal goals.

Yet another option available to a patient using the service is independent study, shown in step S131. Independent study means that a patient logged into the system can use the system to search for general information on a diabetes-related topic (systems for other diseases could have other types of information). The patient could in step S133 look for the desired information in either a frequently-asked-questions webpage or search through the general collection of educational modules, topic by topic. Search tools could be as basic as a general topical outline or as sophisticated as a Boolean logic search program.

If the teaching system gives the patient access to a general informational database such as a diabetes encyclopedia, the patient may in step S135 conduct a search there as well.

Still another search option, as shown at step S137, is a general system search. This feature may be useful where a patient recalls seeing something on the website but cannot remember where. The search could take the form of a text search of all web pages in the web site.

Figure 5:
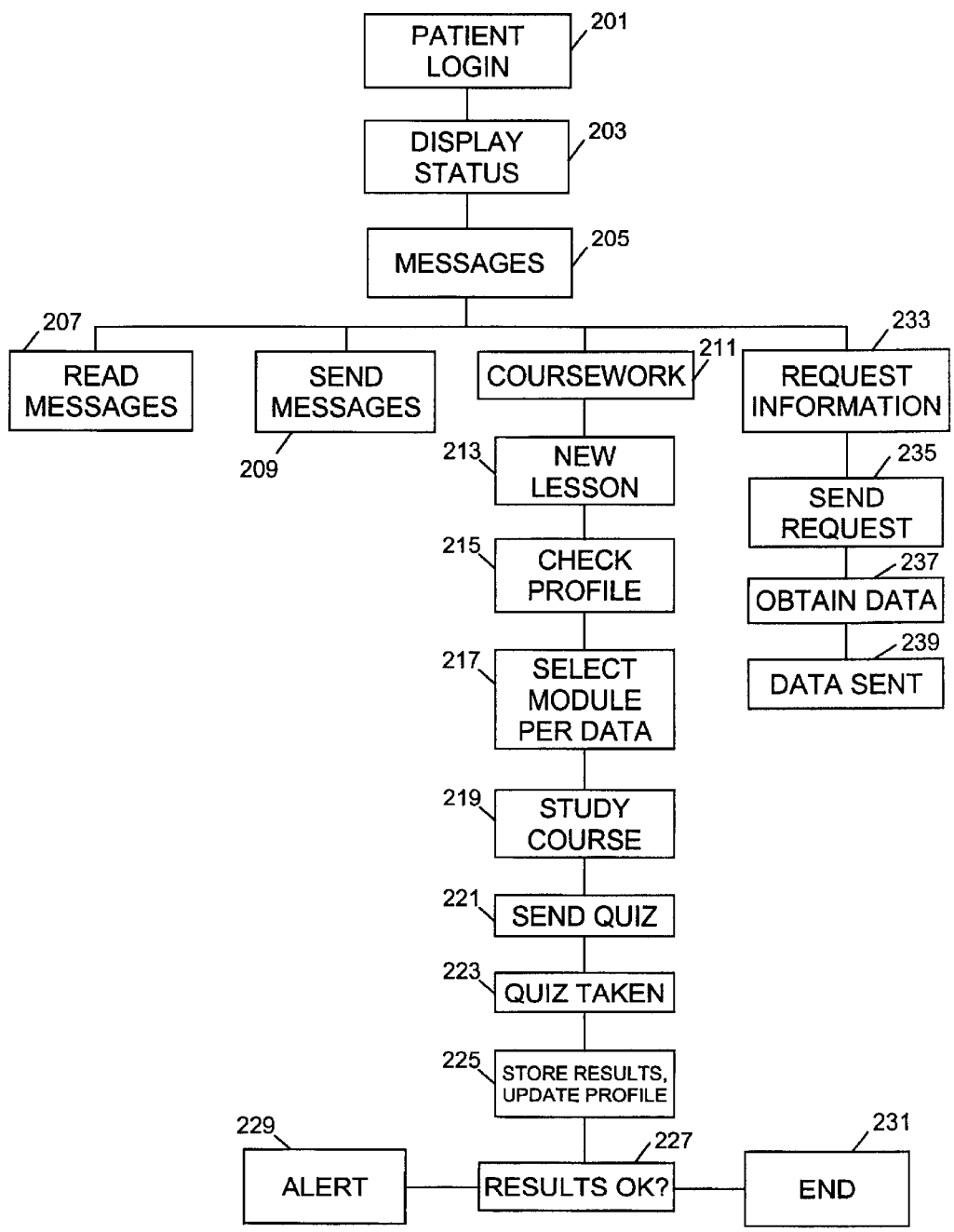
FIG. 5 is a flowchart illustrating an alternate embodiment of the various actions which can be taken as the patient uses the system depicted in FIGS. 1 and 2.

FIG. 5 is a flowchart depicting alternative steps which can be performed when a patient interacts with the computer system used to implement the present invention.

In step 5201 the patient logs into the system by submitting gin name and password. Once the patient is recognized the system can display on the patient's computer (in step S203) the patient's "scorecard" of important vital statistics, along with any other information that is appropriate such as the existence of an upcoming medical appointment.

In step S205 the system can advise the patient that there is a message waiting. This way the patient learns immediately upon login that she has a message, instead of waiting until the patient remembers to check her e-mail.

Following these start-up procedures the patient can then choose either to send and/or receive messages, do coursework, or simply obtain information from the teaching system.

Reading and sending messages, as in steps S207 and S209, can be accomplished using e-mail in the manner already described.

If the patient chooses in step S211 to begin or continue her coursework, the patient sends the teaching system a request in step S213 to receive the next lesson. This request is preferably made electronically over the Internet. After receiving this request the teaching system in step S215 checks the patient's profile information (such information can be kept in a student information database 119 as shown in FIG. 2) to ascertain what lesson the patient should be sent.

The teaching system selects in step S217 the course to be sent to the patient. The precise manner in which the course is selected is discussed else where.

After waiting for the patient to finish her study of the course data in step S219, and upon the patient's request (steps S233 and S235), the teaching system in step S221 sends the patient a quiz corresponding to that course data (steps S237 and S239). After the patient sends the teaching system her answer(s) to the quiz, the teaching system in step S223 grades those answers. In step S225 the quiz results may be stored and the patient's profile updated to reflect completion of the topic; this way, the patient will not in the future be sent the study materials for that topic.

The teaching system checks to see whether the patient has achieved a satisfactory quiz score, and/or has completed reading the study materials in an acceptable time. This is done in step S227. If in step S227 it is found that the patient's performance results are not acceptable, an alert can be sent (step S229). The alert may consist of a message to the patient, CDE and/or physician. If the patient is performing satisfactorily, the process ends at step S231. Optionally, a message of encouragement could be sent.

CDE Use of System

Figure 6:
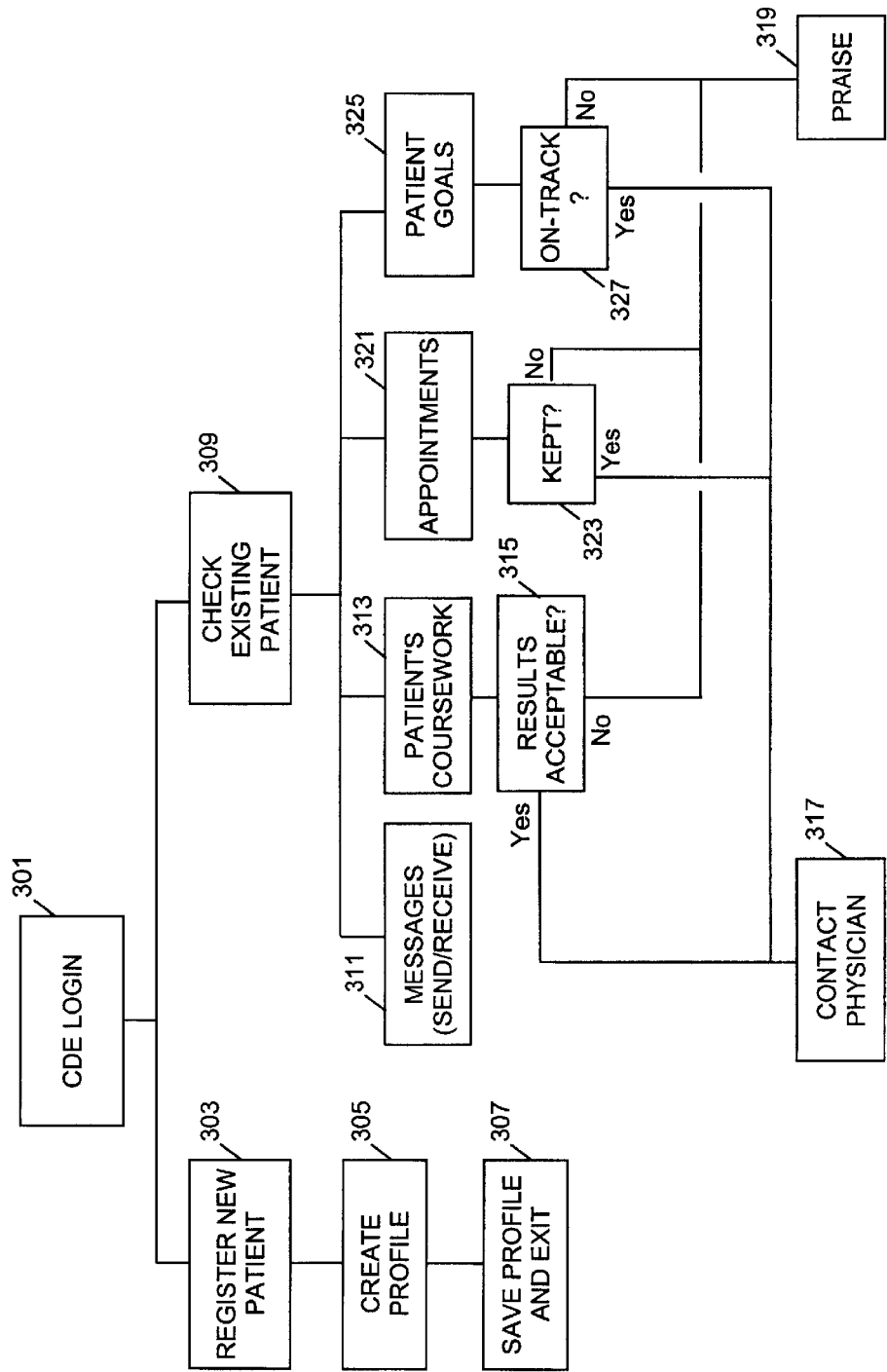
FIG. 6 is a flowchart illustrating various actions which can be taken as the CDE (preceptor) uses the system depicted in FIGS. 1 and 2.

Use of the teaching system by a certified diabetes instruction (CDE) will now be explained in connection with FIG. 6.

The CDE logs into the teaching system in step S301 by submitting a login name and password. Once recognized by the system the CDE can either register a new patient in step S303 or check on existing patients in step S309.

Turning first to registration of a new patient, the CDE creates a profile for the patient in step S305. Creating the profile may include giving the patient a unique login name and associated password, and entering into the teaching system profile information for the patient. By way of non-limiting example, profile information could include the patient's name, address, age, gender, type of diabetes, insulin dosage and so forth. This profile information is stored in a patient profile database such as the student information database 119 depicted in FIG. 2, and is later used by controller 117 to determine what educational material will be sent to the patient.

More specifically, each patient has a profile prepared which characterizes their relevant characteristics (relevant in terms of the goals of the educational system). By way of non-limiting example, a diabetic's profile may include their gender, age, weight, A1c level (also known as glycosalated hemoglobin, which is an indicator of blood glucose level), cholesterol, length of time that they have had diabetes, physical state and so forth. Characteristics indicative of mental state, i.e., depressed, also could be included.

Patient profile information also could be obtained by direct physician or patient input, or from other sources.

It will be appreciated that the CDE also could in step S305 edit an existing patient profile, for example, to reflect a change in medical status or a change in address.

Once the profile is complete the CDE saves that profile and exits, as shown at step S307.

The CDE in step S309 accesses information for an existing patient. Functions available to the CDE include e-mail communication, monitoring of the patient's studies, checking on the patient's medical appointments, and seeing whether the patient is achieving their medical goals. Each of these functions will be discussed in turn.

As shown in step S311 the CDE can send and receive e-mail. Messages can be exchanged with patients and the physician. The CDE can use an available program such as Microsoft Outlook, Microsoft Outlook Express, or Lotus ccMail to handle e-mail.

One of the CDE's responsibilities is to monitor the patient to be sure that the patient is studying the educational materials and taking and performing acceptably on the quizzes provided by this teaching system. In step S313 the CDE can obtain from the system information detailing how the patient's studies are proceeding. Such information can include a listing of educational topics that the patient has studied, the patient's quiz grades and the amount of time spent studying.

Software allows the CDE to monitor how much time the patient spends on each section. Too little time suggests that the patient is only taking the questions—not taking the course. Too much time suggests that the material may be too difficult and prompt a response from the preceptor.

Moreover, if the whole group is taking too much time in one section, then the section may need to rewritten.

At the end of the course, this monitoring allows the CDE to certify that the individual/group has completed the recommended hours of instruction in diabetes self-care knowledge and skills.

If in step S315 the CDE finds the patient's performance is not acceptable, the CDE may then choose to contact the physician in step S317 to decide how to proceed. Alternatively, if the patient's performance is satisfactory, the CDE can in step S319 send the patient a message of praise, or in some other way acknowledge the patient's accomplishment. Such recognition may be a factor in motivating the patient to continue studying.

In step S321 the CDE can check to see whether the patient is keeping all of his scheduled office visits. If CDE determines in step S323 that the patient is not keeping appointments the CDE again can contact the physician in step S317. Patients keeping their appointments can be sent a message of recognition in step S319.

Still another role of the CDE is to monitor the patient to see if the patient is achieving her overall health goals. In step S325 the CDE can check on the patient's health goals and see whether the patient is moving toward or away from those goals (step S327). Patients nearing their goals can be sent a message of encouragement in step S319. If a patient is having difficulty and is moving away from their goal, the CDE can contact the physician in step S317 to work out a course of action.

The foregoing aspects of operation of the present teaching system can be implemented through the use of suitable computer programs, including and not limited to Internet browser and e-mail programs and database management programs. Persistent cookies, Java applets and ActiveX controls all can be used to provide the requisite functions. It is believed that in view of this disclosure such programs could be adapted without further inventive effort to accomplish the goals of the present invention. Group reporting could be implemented by exporting various data fields for each patient such as topics completed to a spreadsheet program such as Microsoft Excel.

Next, particularly preferred aspects of the invention will be described in the context of an interactive adaptive teaching system for diabetics which sends and receives information using the Internet.

With reference now to FIGS. 7A–F, examples are shown of webpages that are sent to diabetic patients using a teaching system in accordance with this invention.

Figure 7A:
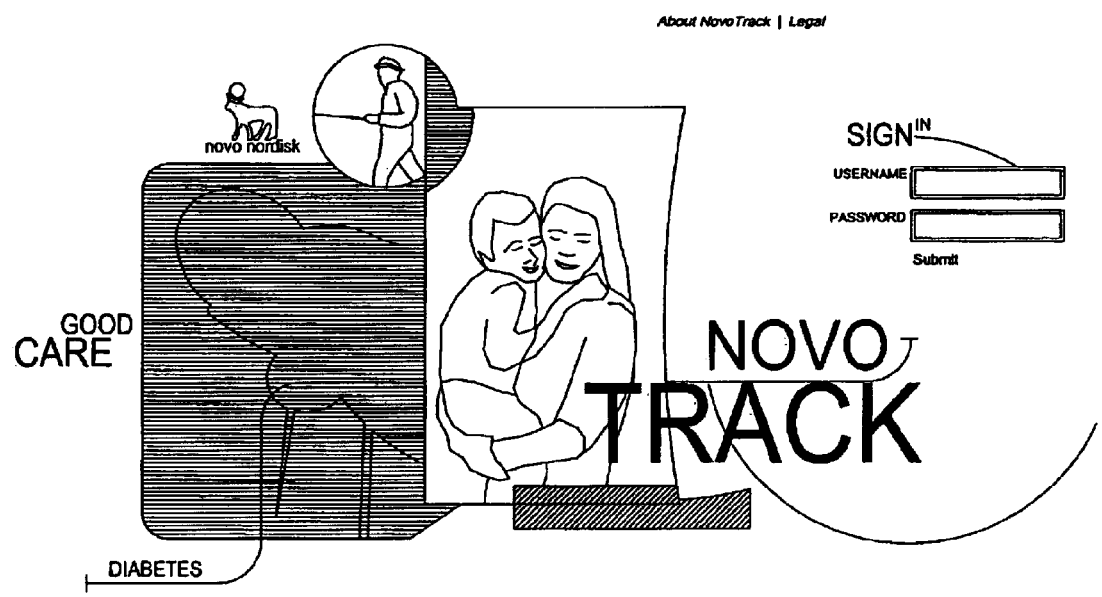
FIGS. 7A–P are "screen shots" of web pages according to a particular aspect of the present invention.

FIG. 7A depicts the initial login page seen by a patient wishing to obtain access to the teaching system. This webpage contains fill-in boxes where the patient can enter their login name and passwords.

FIG. 7B depicts the "main menu" webpage that is displayed once the patient has successfully logged into the teaching system. From the "main menu" webpage the patient can obtain their medical information and access the educational and messaging functions of the system. The webpage has a title section ("Guide to Good Care"), and a personal information section giving information such as the patient's name, physician, important medical facts, and whether the patient has any unread messages. The webpage also includes links to the patient's "Personal Scorecard" and "Message Center". Clicking the link to the "Personal Scorecard" lets the patient obtain their medical information, as shown in FIG. 7F. For convenience, the personal information section is separated from both the "Personal Scorecard" and "Message Center" sections by the main text section. The main text section displays the information associated with the webpage (images also could be embedded therein).

The webpage includes near the top links to a number, here, seven, of "Tracks". Each track corresponds to a general topic, and each track consists of one or more individual articles (previously referred to as educational modules). By way of non-limiting example, Tracks 1–7 are entitled "Getting Good Care", "What is Diabetes", "Healthy Eating & Exercise", "Using Medications Wisely", "Family, Friends & Feelings", "Complications" and "Special Situations". These modules are shown in FIGS. 8A–C and are discussed elsewhere.

To avoid patient confusion, other webpages sent to the patient preferably have the same general layout as the "main menu", and may include a link allowing the patient to return immediately to the "main menu" page.

Figure 7C:
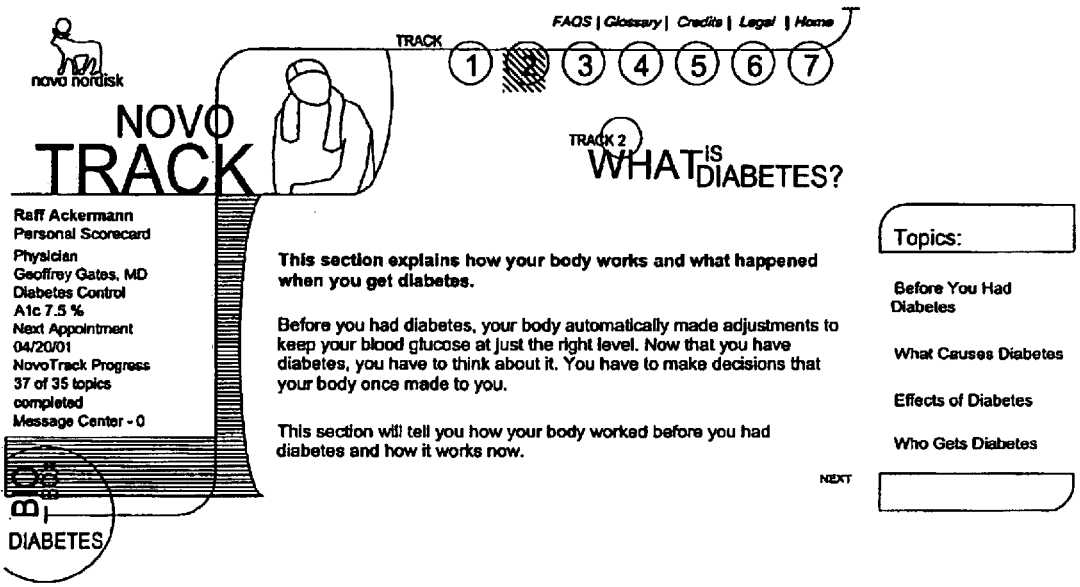

By way of non-limiting example, FIG. 7C depicts the webpage seen by the patient after clicking the link to Track 2. This page, it should be noted, is generally similar in layout to the "main menu" page shown in FIG. 7B. The title of the page has changed to the Track title ("What is Diabetes") and the text portion of the page provides the patient with a discussion of the subject. The webpage includes on the right hand side a "Topics" section containing links to each of the articles which make up the Track, here, "Before You Had Diabetes", "What Causes Diabetes", "Effects Of Diabetes", And "Who Gets Diabetes". Clicking one of these article links will bring up the article.

FIGS. 7D(1–2) depict the article entitle "What is Diabetes". The article text is displayed in the central portion of the web page. Captioned photographs are found to the right of that text. Some of these photographs/captions may include links to other webpages; a link ("See How it Works!") is provided beneath the illustration of a heart in FIG. 7D(2).

A link to the associated questionnaire ("NovoTrack Checkpoint Q & A") is found at the bottom of the article, as seen in FIG. 7D(2). Clicking this link will take the patient to the quiz web page(s).

Figure 7E:
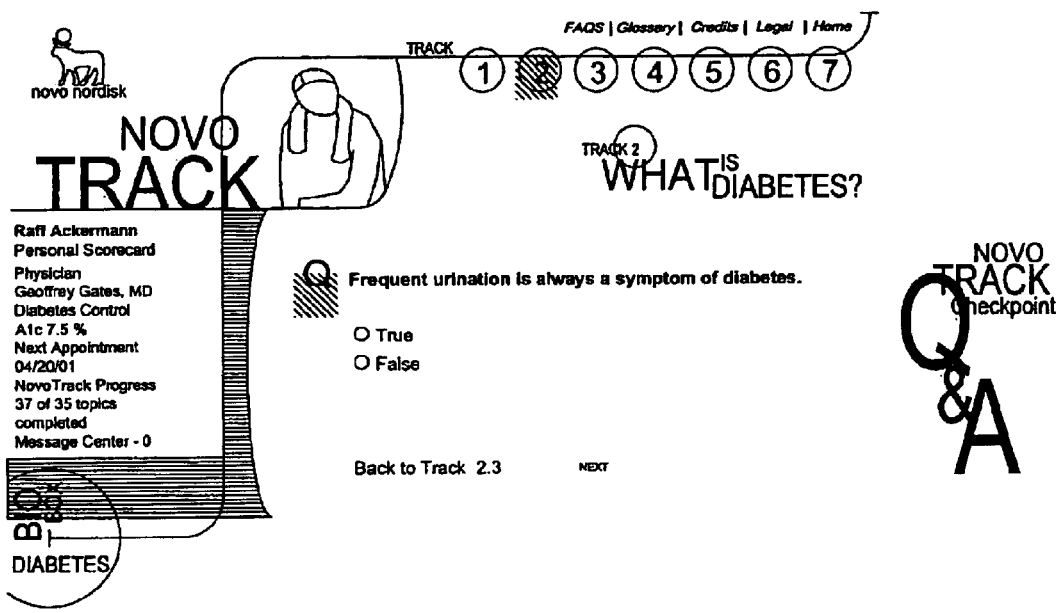
Figure 7F:
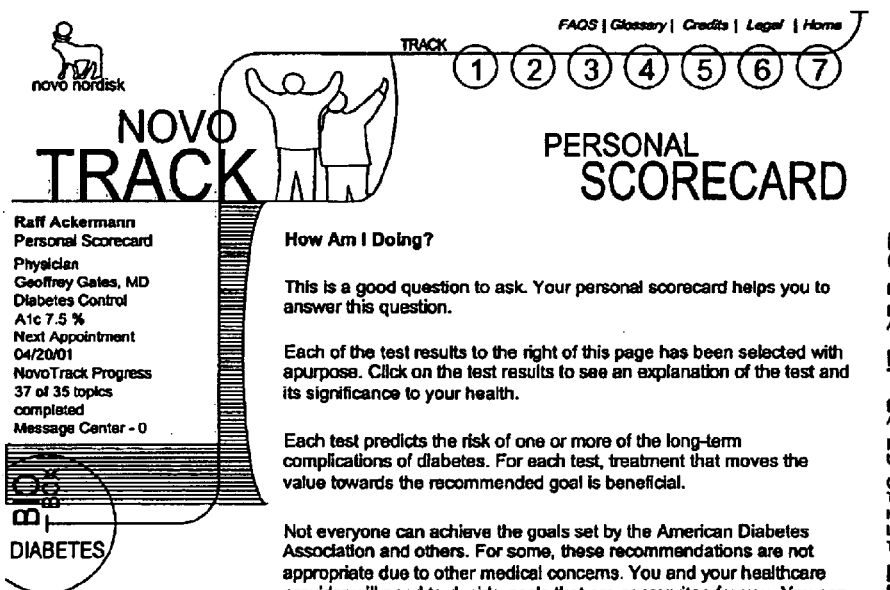

FIG. 7E depicts a sample quiz question. The question is a True/False question, and to answer the user clicks on the appropriate box. Links to the previous page and next question page are provided. As an alternative to the check boxes, drop-down menus could be used.

FIG. 7F depicts the webpage sent to a patient who has clicked a link to access their "Personal Scorecard". The title of the webpage has changed to "Personal Scorecard". The central text portion of the webpage briefly explains what the Personal Scorecard shows. The right-hand portion of the page contains the patient's relevant health data such as cholesterol, blood pressure, lists upcoming medical appointments (i.e., Eye Examination Oct. 25, 2001), and may have links to other information such as Personal Goals. The left hand side of the webpage gives more general information such as the name of the patient's physician, and this information can but need not be shown on other webpages as well.

Also found at the top of the "main menu" page are links to FAQs (frequently-asked questions), a glossary, credits, legal information and a home page.

If desired, a short, annotated list of major organizations that provide reliable information about diabetes could be included. Examples are MayoHealth, the American Diabetes Association, American Association of Diabetes Educators, and the National Institutes of Health (NIDDK).

With reference now to FIGS. 7G–P, examples of webpages which can be accessed by the CDE when using this invention are depicted.

Figure 7G:
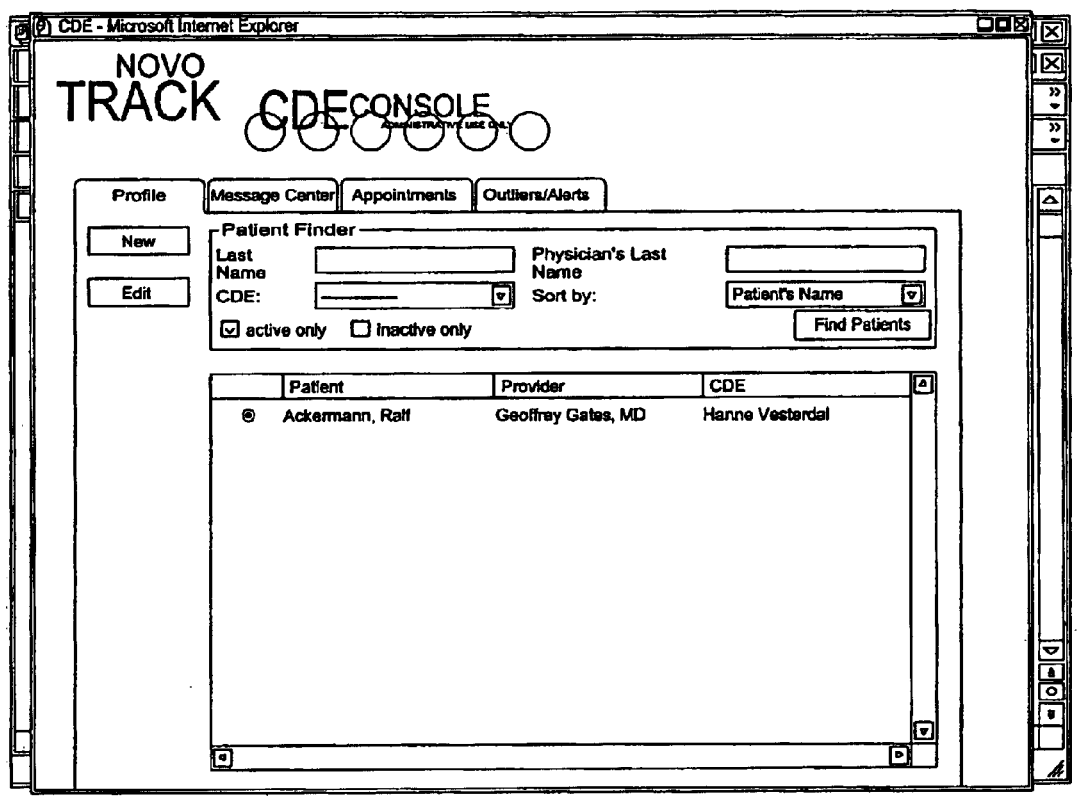

FIG. 7G depicts the "main menu" webpage which is displayed immediately after the CDE has successfully logged into the teaching system. The webpage gives the CDE a choice of operations such as "Profile", "Message Center", "Appointments", "Outliers/Alerts" and "Outline", each of which will be explained hereafter. By clicking on these tabs the CDE can access the functions associated with each tab, as will now be explained. If desired, links to other websites could be included, such as a link to the system administrator. Other webpage formats such as drop-down menus could be used in place of the tabs.

FIG. 7G shows the webpage for "Profile". Clickable tabs and drop-down menus allow the CDE to add a new patient user profile, edit profile information for existing patients, search for patients, sort patients by name or physician name, and displays a list of patients. Clickable check boxes can be used to mark the patient whose profile is to be altered, or whose information the CDE seeks to review.

Figure 7H:
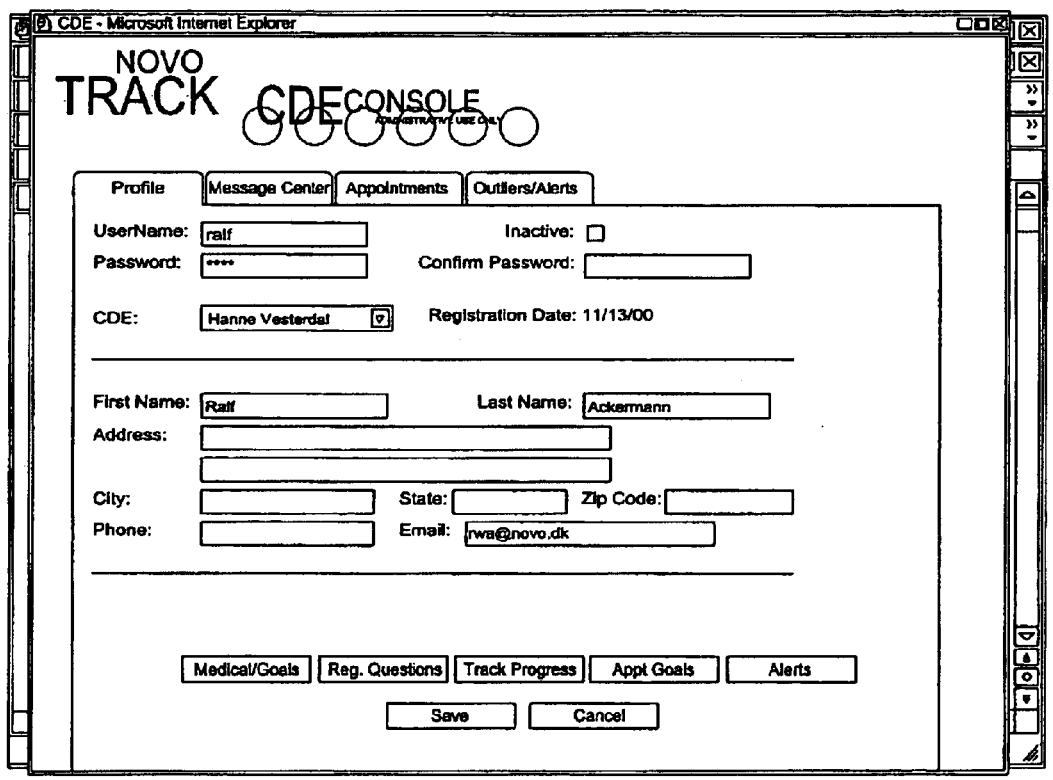

FIG. 7H depicts the webpage as the CDE would see it after clicking the "Profile" button. The displayed webpage allows the CDE to add a new patient or edit an existing patient profile (if the CDE wishes to edit an existing profile the fields already will be filled-in). The CDE can input general profile information into the appropriate fields, such as user name, password, CDE name, patient address, and so on. Some fields may be drop-down menus, others, fillable boxes and/or check boxes. From this page the CDE also can monitor existing patients.

The webpage shown in FIG. 7H has a number of buttons ("Medical/Goals", "Reg. Questions", "Track Progress", "Appt Goals", "Alerts") which when clicked allow the CDE to input still more information and check patient status. These buttons will be discussed in turn. "Save" and "Cancel" buttons are also provided.

Figure 7I:
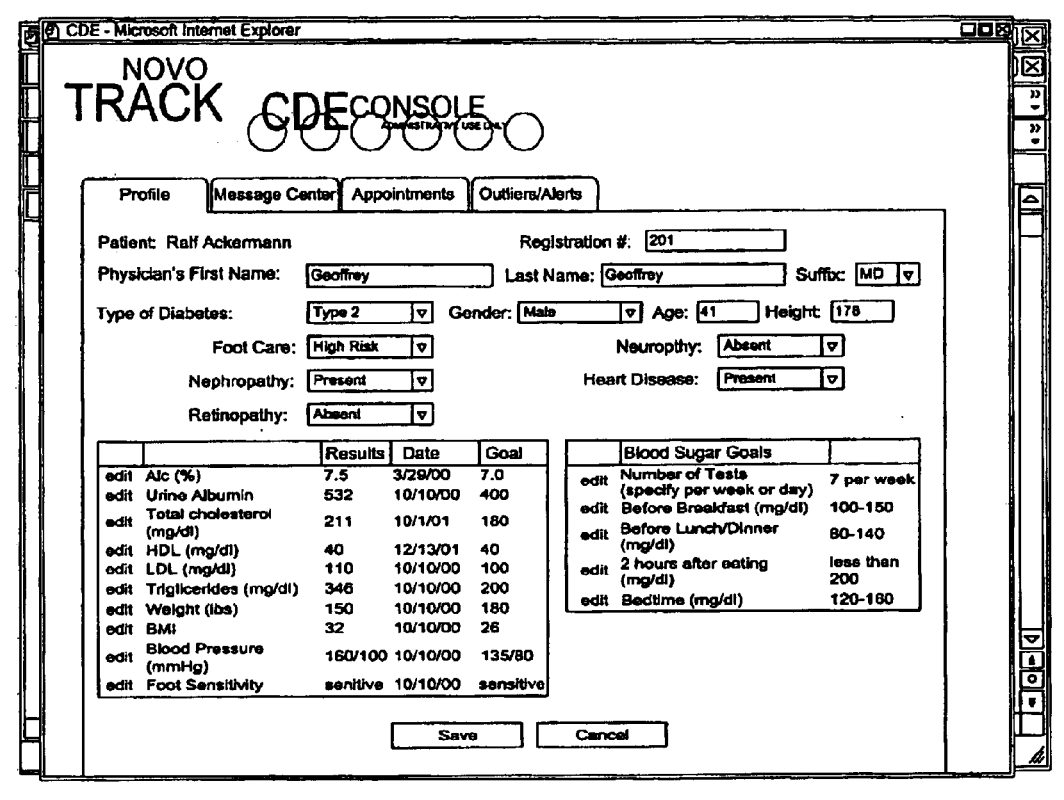

When the "Medical/Goals" button is clicked, the webpage shown in FIG. 7I is displayed. Various items of profile information such as patient name, physician name, type of diabetes and so forth are set out in the top portion of the page. Some, none or all of these items can be editable, whether by direct input into the field or drop-down menu. The lower portion of the webpage contains medical information; as shown in FIG. 7I, there are two tables, the one on the left containing test results, the one on the right showing blood sugar goals (blood glucose also could be used). The test table lists the name of the test, the patient's most recent results, the date of the test and a goal. Each entry in the table has an associated "edit" button which when clicked lets the CDE alter the values for that entry. Similarly, the blood sugar goal table lists a number of values such as the number of tests or specific test times, and an associated goal such as a number of tests or a blood glucose reading. Again, entries in the table have associated "edit" buttons which when clicked lets the CDE alter the table entries. "Save" and "Cancel" buttons are provided.

Figure 7J:
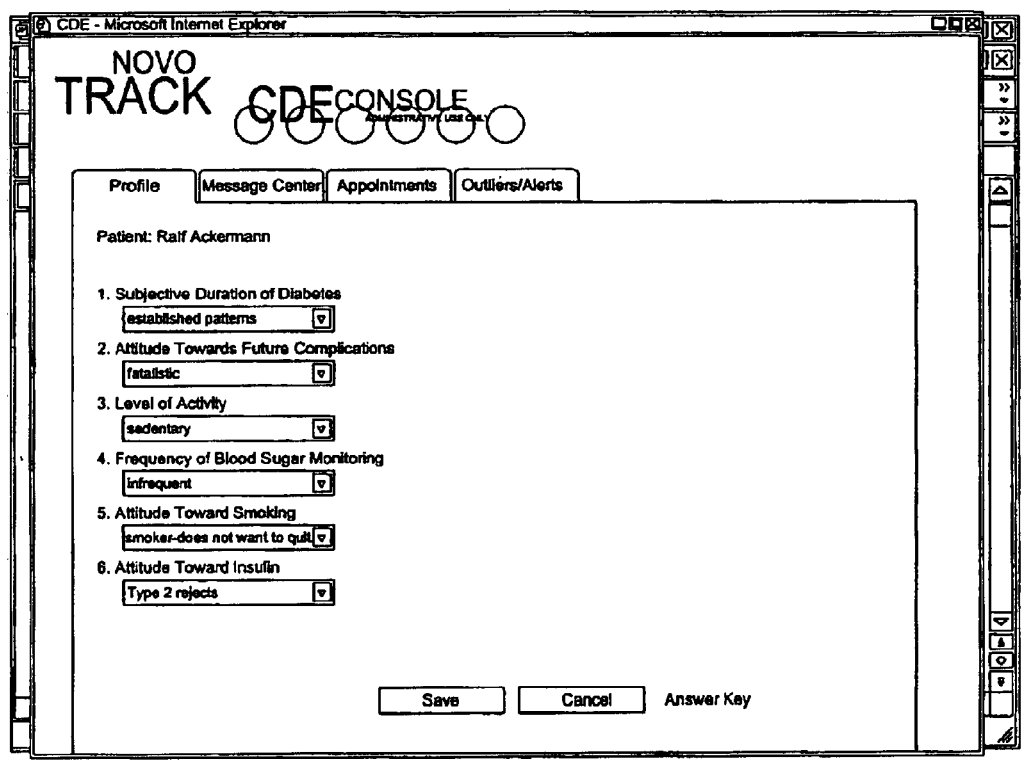

FIG. 7J shows the webpage that is displayed when the CDE clicks the "Reg. Questions" button on the Profile webpage of FIG. 7H. As depicted in FIG. 7J, the webpage sets forth a number of general medical questions to be answered by the CDE on the basis of their knowledge of the patient's medical condition. For convenience, answers to these questions are provided using drop-down menu choices, but fill-in boxes also could be used. By way of example, Question 3 requires the CDE to specify the patient's level of activity. As shown in FIG. 7J, the CDE has specified that the patient has a sedentary level of activity. An "answer key" link is provided which allows the CDE to obtain more information about the questions asked and the possible answers. "Save" and "Cancel" buttons are provided.

FIG. 7K shows the webpage which the CDE sees after clicking the "Track Progress" button on the main webpage of FIG. 7H. This webpage displays information which the CDE can use to monitor the patient's study efforts. The webpage includes a table listing by number and name each topic in the course of study that the patient has completed, the date the patient completed the topic, the amount of time the patient spent displaying (and presumably reading) the topic, and the number of questions in the associated quiz which the patient answered correctly.

After clicking the "Appt Goals" button shown in FIG. 7H the CDE sees the webpage depicted in FIG. 7L. This webpage displays the dates of the patient's most recent and next physician's and ophthalmologist appointments (other types of medical appointments also could be listed). The CDE can enter or modify the date information by entering data in the appropriate fill-in field. Alternatively, drop-down menus or other date-input schemes could be used. "Save" and "Cancel" buttons are provided.

Figure 7M:
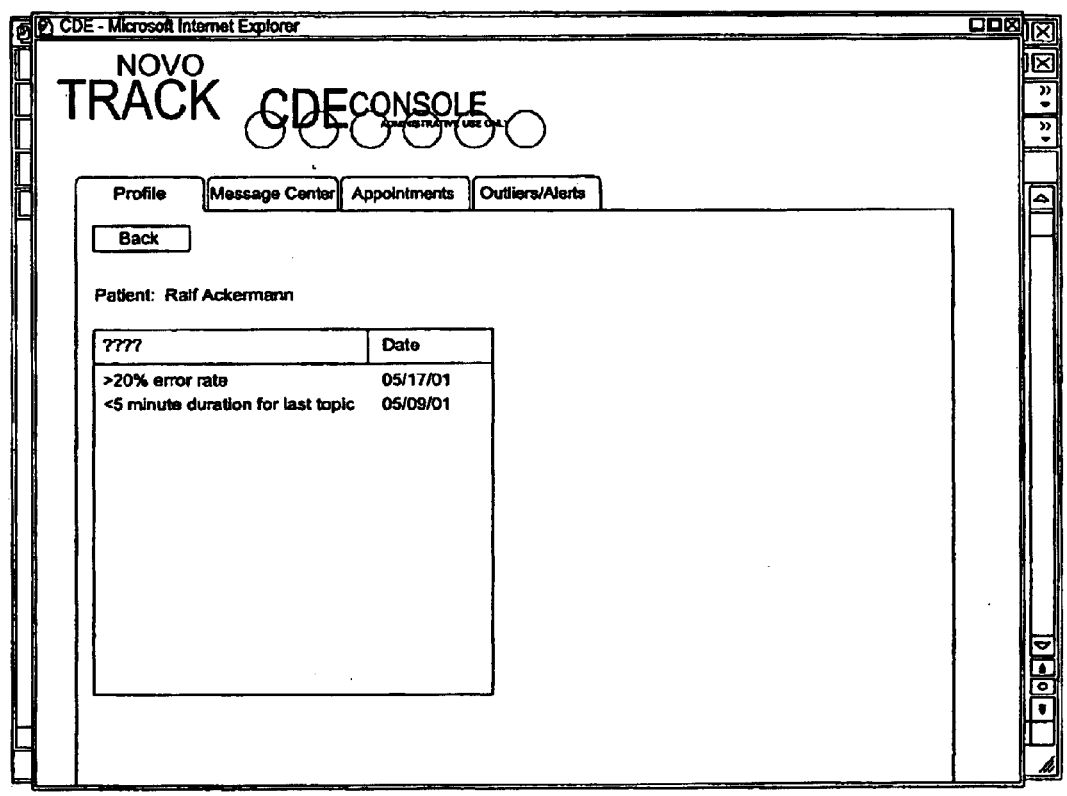

FIG. 7M shows the webpage sent to the CDE when the CDE clicks the "Alerts" button shown in FIG. 7H. This webpage displays any situations which may be of concern, such as a low quiz score or spending too little time studying.

Figure 7N:
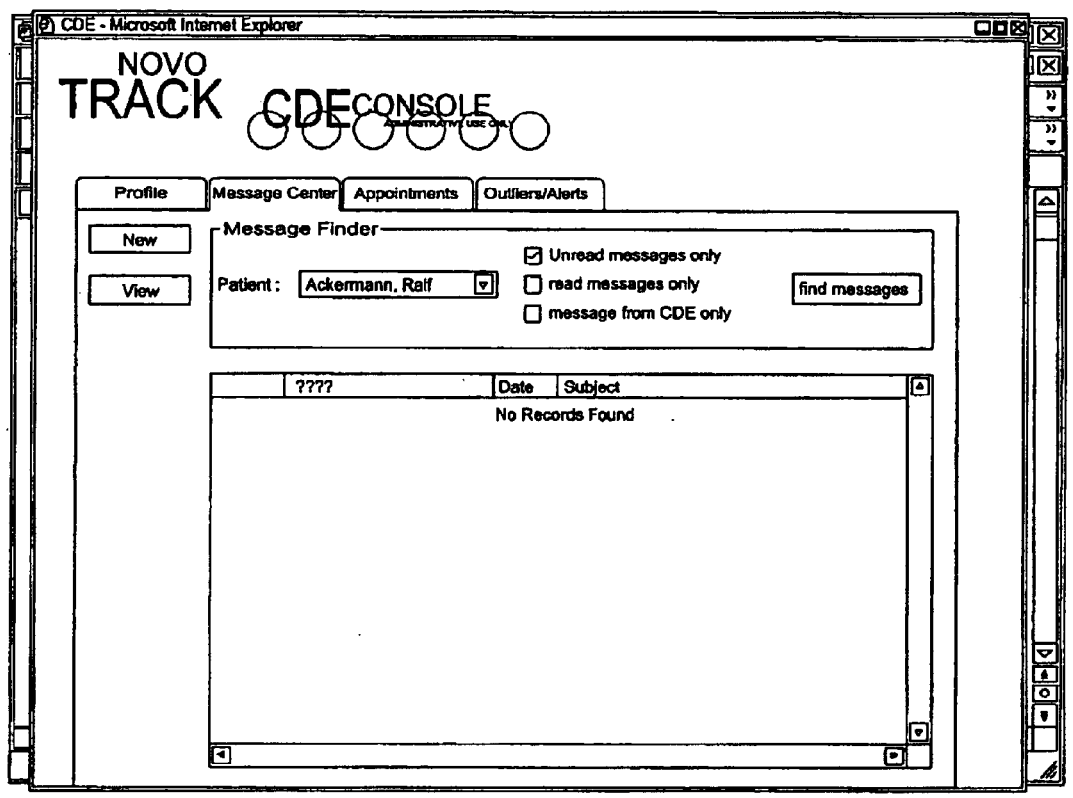

FIG. 7N shows the main menu page of FIG. 7H when the "Message Center" tab is clicked. Drop-down menus allow the CDE to check whether they have received e-mail from any particular patient. A "New" button allows the CDE to generate and send a new message. Messages can be filtered by clicking checkboxes such as "unread messages only".

Figure 7O:
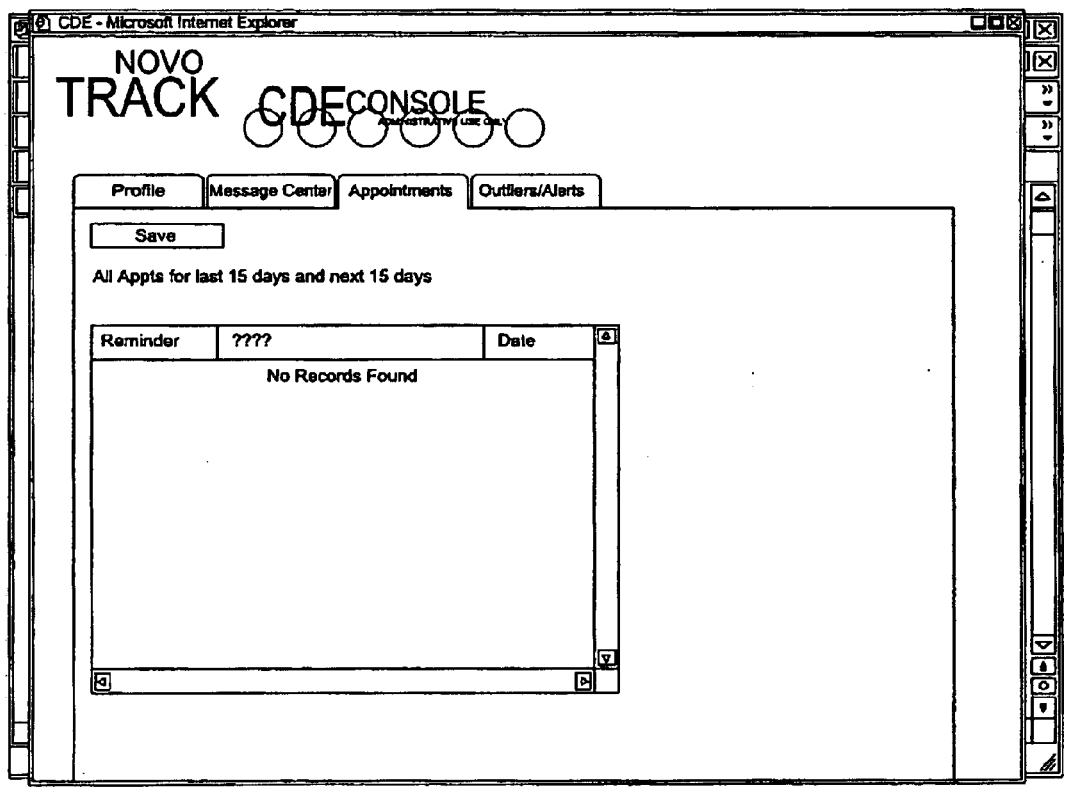

FIG. 7O shows the main menu page of FIG. 7H when the "Appointments" tab is clicked. The webpage includes a table listing both previous and upcoming appointments for the patient.

Figure 7P:
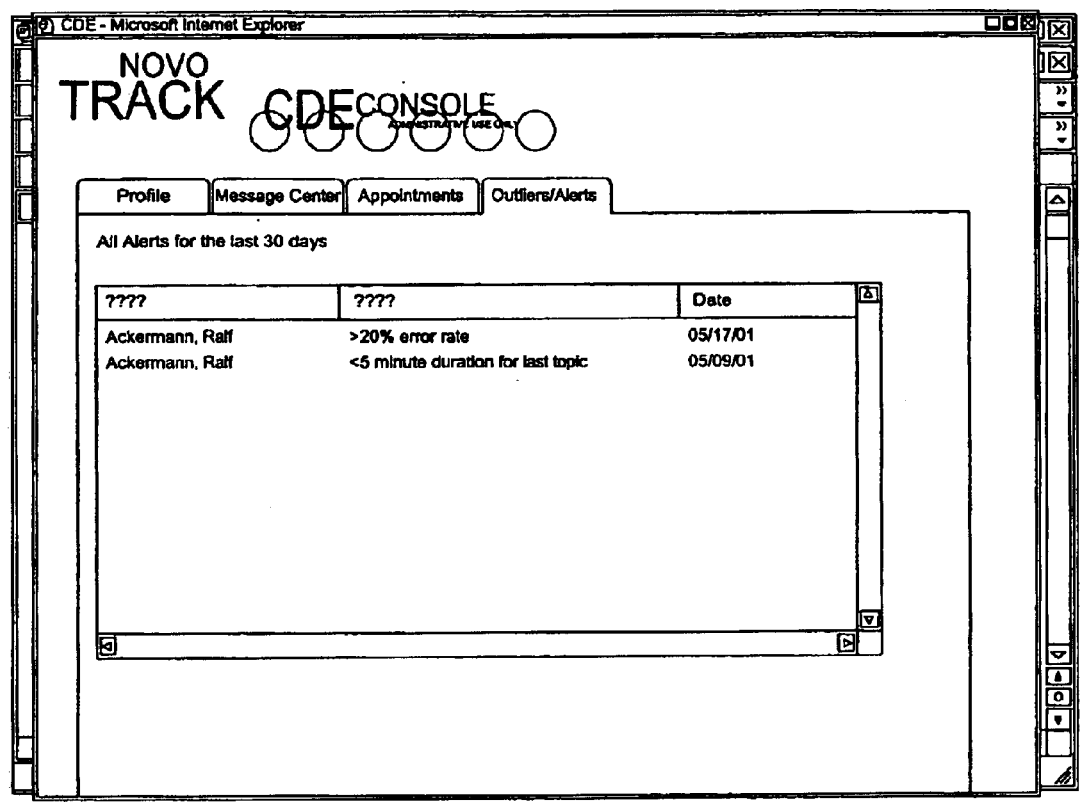

FIG. 7P shows the main menu page of FIG. 7H when the "Outliers/Alerts" tab is clicked. The webpage includes a table displaying the name of any patient for which there is an alert, the nature of the alert, and the date of the alert.

Clicking the "Outline" link on FIG. 7H takes the CDE to the content matrix shown in FIGS. 8A–C. This content matrix lists all of the educational modules which can be sent to patients as part of their program of study As previously explained, at least some educational modules in the content matrix are written from several perspectives. Certain educational modules will be appropriate for some patients but not for others. For example, a young female with diabetes would be given an educational module on preparing for pregnancy that would be irrelevant to a male. The controller software allows choices from among a large number of different topics or similar topics written from different perspectives. Thus, a male with type 2 diabetes and a history of a myocardial infarction will be given different educational modules than a female with type 1 diabetes who is planning on having children.

With continued reference to FIGS. 8A–C, a detailed content matrix having all of the course modules that the teaching system may use is shown. The matrix is divided into seven "tracks" (other numbers of tracks could be used), a track being a general subject of the curriculum such as "Getting Good Care". Each "track" corresponds to one of the tracks that is displayed on the webpages accessed and viewed by the patient, such as the tracks which are shown in FIGS. 7B and 7C. Sections are uniquely identified within the content matrix using a hierarchical scheme; the leftmost character corresponds to the track, the character to the right thereof corresponds to the topic number within the track, and the character to the right of that (if used) signifies that the section is one of several alternative subsections. More specifically, section 6.2b corresponds to Track 6 ("Complications"), topic 2 ("Neuropathy"), subsection b ("Treating Neuropathy"). By way of non-limiting example, it will be appreciated that section 6.2b only would be displayed for a patient whose profile shows neuropathy is present, since diabetics presently free from neuropathy would not find this subject to be of interest.

Grouped within each track are a series of educational modules corresponding to all of the different topics that fall within the track. Each educational module has a series of associated questions. As explained in detail hereafter, some educational modules share common titles, although their content is at least in part different. It is by provision of these modules that the present invention allows the education process to be tailored to reflect the individual patient's profile.

With continued reference to FIGS. 8A–C, the teaching system includes a computer program which first obtains the patient's profile data and then selects educational modules from the content matrix on the basis of such data. Some educational modules will be displayed for all patients, such as module 2.1 ("Before You Had Diabetes"). Others will be sent to a subpopulation of patients. By way of non-limiting example, the computer program will determine whether a patient accessing track 2 is to be given access to modules 2.2a or 2.2b (both entitled "What Causes Diabetes"); module 2.2a contains information that will be of interest to patients having Type 1 diabetes, whereas module 2.2b contains information that will be of interest to patients having Type 2 diabetes. Thus, modules 2.2a and 2.2b contain different information, and the teaching system will determine which of the two modules to send to the patient according to the kind of diabetes (Types 1 or 2) indicated in the patient's profile.

By way of non-limiting example the program could be written using Fortran or any other suitable programming language. Any program able to select an education module(s) from a content matrix of education modules on the basis of patient profile information can be employed.

While the foregoing discussion of this invention emphasizes its use with the treatment of diabetes, it will be appreciated that this invention is of general applicability and can be used for any disease requiring patient education and/or monitoring. By way of non-limiting example, courses of study could be developed to help care for patients suffering from diseases such as AIDS, multiple sclerosis, coronary illness, eating disorders, mental illness and so on.

Those skilled in the art will understand that many variations on the above-mentioned webpage layouts could be used without departing from the scope of this invention. Different information and different formats could be employed. Fill-in sections and drop-down menus could be changed.

Aspects of the present invention relating to the remote evaluation of the nutritional content of a patient's meal by a healthcare provider will now be described with reference to FIGS. 11A and 11B.

Diabetic patients requiring insulin must adjust their insulin dose, in part according to the amount and type of food which they consume. As part of their education process, diabetics are taught by their CDE (or other healthcare professional; the term CDE is used here by way of example and not limitation) how to estimate the nutritional content of the foods they eat. The CDE teaches the patient that to estimate nutritional content the patient must first determine the quantity of each type of food being eaten, and then figure out the nutritional value for that food. By adding together all of the estimated nutritional values for the foods to be eaten, the patient can then obtain the complete nutritional value of their meal. Thus, a diabetic having a bowl of cold cereal for breakfast would first figure out the amount of dry cereal in the bowl and the amount of milk that has been added, and then figure out the nutrition in the cereal and the milk. To obtain the overall nutritional information, the nutritional figures for both the cereal and the milk are added.

The nutritional information for different types of food is widely available in tabular form, This means that once the patient knows the amount of each type of food which is before them, they can easily figure out the total nutritional content of all that food.

Determining the amount of food in a meal is not easy. While this skill can be learned with training and practice, such training may be time consuming and labor intensive. Owing to time and budgetary limitations, it is usually not possible to teach diabetics how to analyze every type of food that they typically consume. Conversely, it would not be efficient to teach a patient how to judge foods they are unlikely to consume, i.e., it would not be practical to teach a vegetarian to analyze meat. It also would not be efficient to teach a patient how to judge foods they are unlikely to encounter.

Nevertheless, there may be situations where a diabetic may have to analyze foods that they were not trained to evaluate. For example, the diabetic might, when dining out, be faced with foods of unfamiliar type, or the patient simply might want to try something different for a change.

Thus, while a diabetic patient may as part of their diabetic education process learn how to estimate the portion size of various types of foods, it is likely there will be many instances where the patient is faced with types of foods that they have not been trained how to evaluate. In such situations it would be helpful if the diabetic patient could contact the CDE to learn how to judge such foods. Because offering constant and immediate CDE access is costly, present diabetes care programs do not provide patients with such direct CDE access.

Accordingly, the present invention provides the diabetic patient with improved access to their CDE, and with a system that allows the patient to send their CDE images of the food that the patient is about to eat, or which the patient has just eaten. This way, the CDE can advise the patient how much and what are the nutritional properties of the food they will eat (or have just consumed).

It is envisioned that direct patient access to their CDE can be facilitated by providing the patient with a small digital camera that allows them to take unobtrusive pictures of their meal, and a system for sending the digital picture over the Internet to the CDE for analysis. In this way the CDE will always be able to help the diabetic patient evaluate their meals before the meals are eaten.

As an alternative to having the patient's CDE be "on-call" at all times to help estimate food portions and answer questions, after certain hours, say, 8AM-6PM, the patient's inquiries could be routed to a covering CDE working a shift outside those hours. Depending upon the time, one covering CDE might be able to respond to questions from several other CDEs.

Incidentally, while it is presently thought to be preferable to have a CDE available to answer questions in "real-time", a delayed response also could be provided. In that case, it may be preferable to arrange the system so that the patient does not wait more than a predetermined amount of time, say, half an hour, or even to send the patient a message advising when they can expect to receive a response to their inquiry.

Figure 11A:
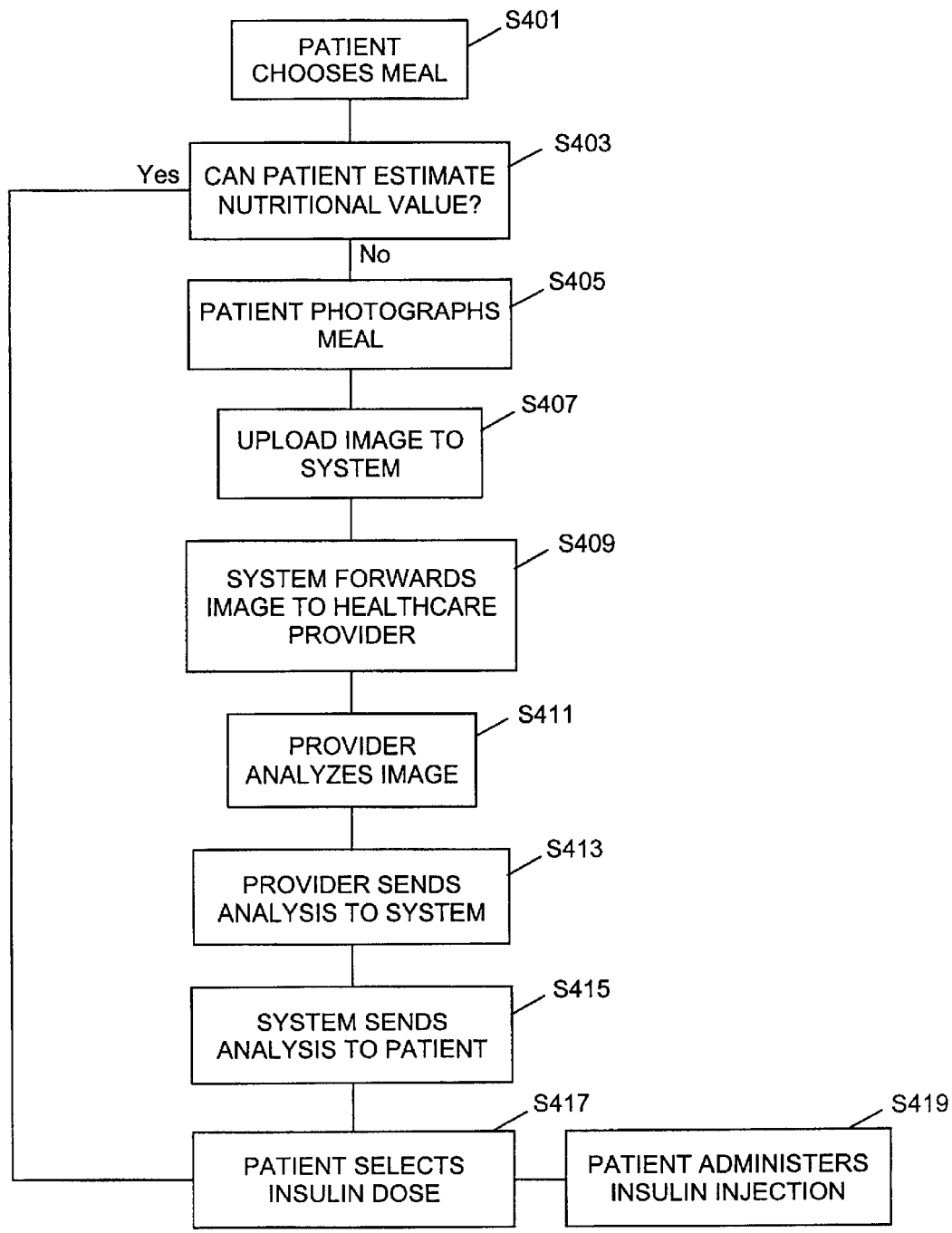
FIGS. 11A and 11B are flowcharts depicting systems which allows a patient to send image data to a healthcare provider and receive appropriate information back from the healthcare professional.

With reference now to FIG. 11A, the patient chooses their meal in step S401. If in step S403 the patient determines he or she can estimate the nutritional value of the meal without assistance, then in step S417 the patient selects the appropriate amount of insulin for injection based in part upon such nutritional value, also taking into account such other factors as weight and exercise level as is appropriate. The patient then administers that dosage in step S419.

Should the patient be unable in step S403 to estimate the nutritional value of all or just a part of the meal, the patient can then in step S405 use a digital camera (not shown) to take a photograph of all or part of the meal that can be sent to the healthcare provider. The term "photograph" is used in the general sense, and prefereably refers to a photograph in which image information is stored in digital form. Other information could be provided in place of or along with the image information, such as weight or temperature.

While any suitable digital camera can be used, it is presently thought to be preferable to employ a compact digital camera. This way, a patient dining in public will be able to photography their meal without attracting undue attention. By way of non-limiting example, digital cameras such as the camera modules which can be added to personal digital assistants (PDAs) such as the Handspring® Visor are thought to be preferable. One example of such a camera module is the eyemodule2, available from PalmGear HQ of Arlington, Tex. The eyemodule2 allows users to take color pictures which can be sent to others by e-mail.

Another non-limiting example of a digital camera that could be used with this invention is a digital camera contained in a wristwatch, such as the Casio Wrist Digital Camera Watch, model no. WQV-1-BNDL, although owing to limitations imposed by its size, this camera may not perform as well as the eyemodule2.

In a further embodiment of this invention, the digital camera can be integrated into any suitable device likely to be used by the diabetic patient, such as a blood glucose monitor or blood pressure meter. Since most diabetic typically carry a blood glucose monitor with them, this is a good way to insure they carry the digital camera as well.

Still another option for sending the meal images to the healthcare provider is to employ a PDA capable of sending e-mail and having a camera module as already described. This way, the patient could immediately after having taken the picture of their meal compose a suitable message and forward the message and the photograph directly to the healthcare provider by e-mail. Moreover, if the PDA is web-enabled, the image could be uploaded to the healthcare provider over the Internet in the manner already described.

Any other suitable web-enabled device or device capable of sending a digital image file from the patient to the healthcare provider, whether now known or hereafter developed, also could be used.

Meal pictures could be taken in any manner which allows the healthcare provider to evaluate the nutritional content of the meal. Any or all of one or more pictures of the entire meal, individual courses in the meal, or even individual dishes in each course could taken.

Once taken, the digital picture(s) of the meal are then in step S407 uploaded and sent via the Internet or e-mail to an adaptive interactive preceptored teaching system such as that already described. Such uploading can be effected in known manner, for example, first by transferring the image data from the digital camera via a USB (uniform serial bus) connection to a personal computer, and then by sending the image data from the personal computer to the healthcare provider's computer via the Internet. By way of non-limiting example, an Internet website having webpages along the lines shown in FIGS. 7A–P could include an appropriate link which, when activated by the patient, would send the patient to a screen prompting the patient to upload the meal images, say, by asking the patient to browse and identify the file to be uploaded to the web site and then, after the file has been identified, requesting the patient to click a suitable link to have the file be sent on to the website. A suitable acknowledgment of receipt of the uploaded image file could be returned to the patient via either the Internet or e-mail.

Alternatively, the meal images could be sent in known manner to the healthcare provider as attachments to e-mail.

Having received the digital image from the patient, the system in step S409 forwards the image(s) to the diabetic patient's healthcare provider for analysis. Optionally, the patient could include a message with the picture.

In step S411 the healthcare provider analyzes the digital picture(s) of the patient's meal to determine portion size and, if it is desired to check the patient's own estimate based upon that portion size, nutritional content. The healthcare provider then sends their analysis of the meal to the adaptive interactive preceptored teaching system in step S413. The adaptive interactive preceptored teaching system passes that information on to the diabetic patient in step S415 and, if desired, can record this information in the patient's profile (not shown). If desired, the patient can as part of the education process be sent an explanation of how the nutritional value of the meal was determined.

In step S417 the diabetic patient selects their insulin dose according to the determined nutritional value of the meal, and administers that dosage in step S419.

The foregoing system also can be used by a patient whose diabetes does not require insulin. To care for themselves, such a patient strives to eat balanced meals having the same general nutritional value, so that their nutritional intake stays approximately constant. This can help to avoid fluctuations in blood glucose level that might occur were the patient to have less regular eating habits.

In this embodiment, the provider might advise the patient not only of the general nutritional content of their meal, but also might suggest how the meal could be modified to reflect the patient's own needs. By way of non-limiting example, if the a patient ordinarily consuming about 600 calories per meal is about to consume a meal containing approximately 500 calories, the healthcare provider might suggest the patient add additional food such as a suitable dessert to increase the meal by some 100 calories. Likewise, if the patient's meal nutritionally unbalanced, say, too high in fat, the healthcare provider might suggest an alternative such as having toast with marmalade instead of buttered toast.

It will be appreciated that this invention also could be employed by nondiabetics who wish to monitor their diets. By way of non-limiting example, people desiring to lose or gain weight could use this invention to monitor their caloric intake.

Figure 11B:
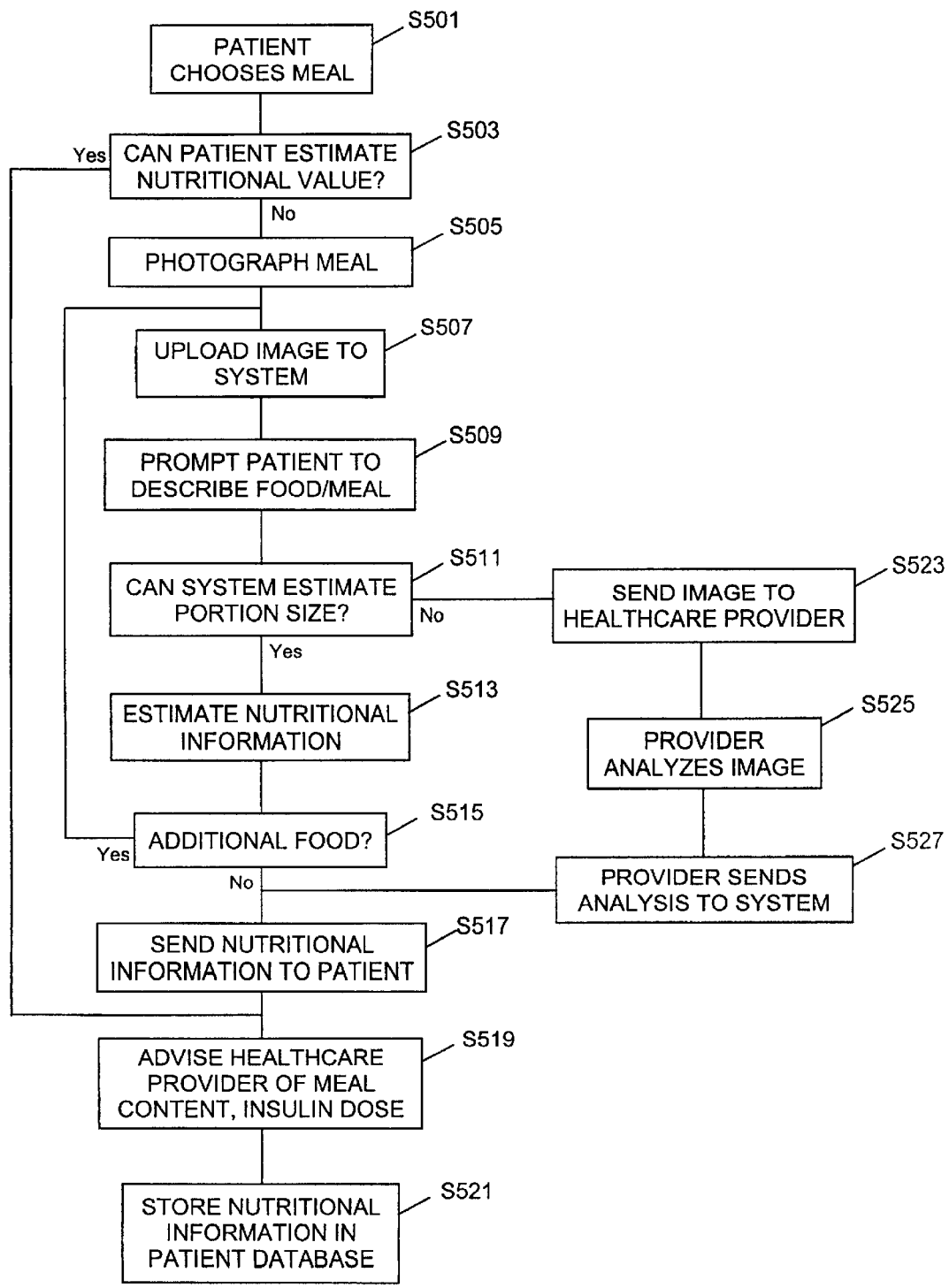

Another embodiment of the present invention is depicted in FIG. 11B. This embodiment differs from that just described in that the system prompts the patient to describe their meal. The system also provides for automatic intelligence (AI) estimation of the food, and, where the system cannot analyze the food, analysis by a healthcare provider.

In step S501 the patient chooses their meal. If in step S503 the patient can estimate the nutritional value of their meal, then the patient in step S519 uses the system to advise their healthcare provider of their meal's nutritional content and the insulin dose which has been administered.

Should the patient be unable to estimate the nutritional value of their meal, then the patient photographs the meal in step S505 in the manner already described with regard to the previous embodiment. The image of the food/meal is uploaded to the system in step S507, and the patient is in step S509 prompted to describe the food or meal (i.e., "grilled chicken breast and rice"). If in step S511 the system is able to estimate the size of the portion of food in question, then in step S515 the system ascertains whether more food is present to be analyzed. If there is, then the process loops back to step 507, where an image of this other food is uploaded to the system for analysis as already described.

Once the system has analyzed all the food, the nutritional information for that food is estimated in step S513. The system can in step S515 ask the patient whether there is any other food, and if there is, a fresh image of that other food is uploaded to the system in step S507 and the analysis of the food by the system is performed in the manner already described. Once all the food has been analyzed in step S515 (answer "no" to additional food), the nutritional information is sent to the patient in step S517. The system also advises the healthcare provider of the patient's meal content and insulin dosage in step S519, and that information can be stored in a database corresponding to that patient, in step S521.

Should the system be unable in step S511 to estimate the portion size of the meal, say, because the image uploaded to the system in step S507 is of poor quality, then the image is in step S523 sent to the healthcare provider. The healthcare provider analyzes the image in step S525, and sends the results of that analysis back to the system in step S527.

At this point, the nutritional information is sent to the patient in step S517 and the process advances in the manner already described.

The precise manner in which the system recognizes in step S513 the portion size is not important; any type of object recognition software, whether now known or hereafter developed, could be used, to evaluate the size and, optionally, nature of the food.

Figure 12:
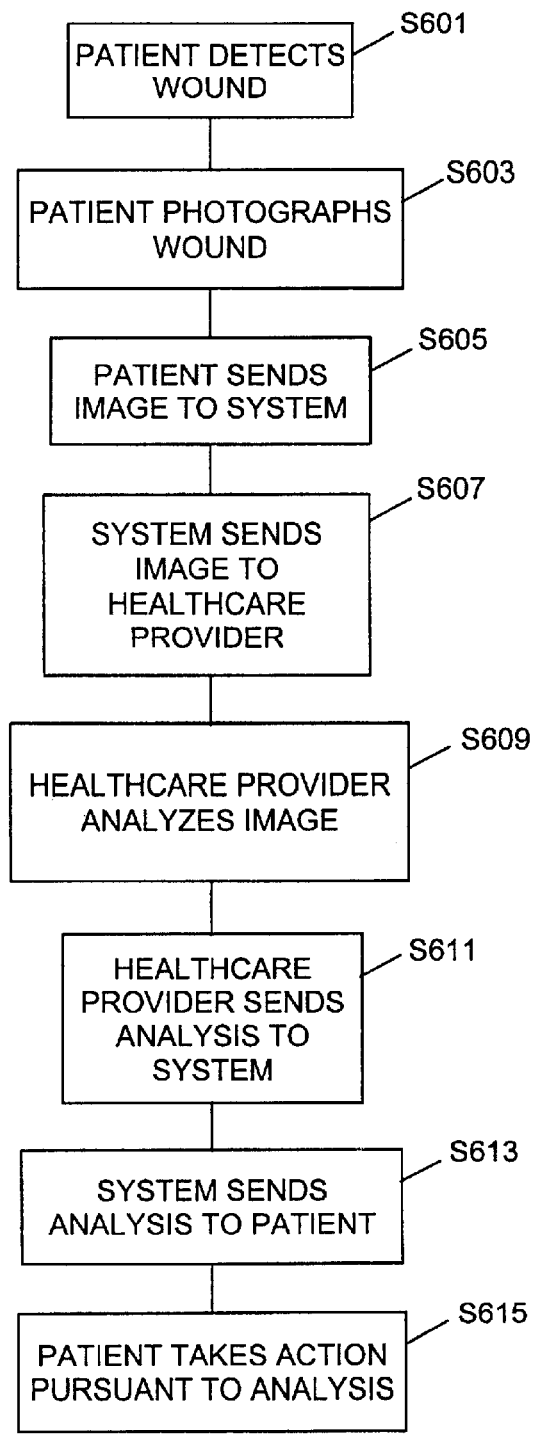
FIG. 12 is a flowchart showing a system through which a patient can send an image of a wound to a healthcare provider for analysis.

A further embodiment of this invention, as depicted in FIG. 12, can be used by a diabetic patient who, having discovered a wound on their body, needs to show the wound to a healthcare provider so that the healthcare provider can evaluate the severity of the wound and determine what care is appropriate. In particular, this aspect of the invention could be used to evaluate diabetic neurotropic ulcers. By way of non-limiting example, this system might be of particular interest to those living in remote locations, where seeing a healthcare provider is difficult.

With reference now to FIG. 12, the patient in step S601 detects a wound. The wound is photographed by the patient in step S603, and the image of the wound is sent in step S605 to a monitoring system such as the adaptive interactive preceptored teaching system already described. The system sends the image in step S607 to the patient's healthcare provider, who analyzes the image in step S609. The healthcare provider sends their analysis to the system in step S611, and the system forwards the analysis to the patient in step S613. In step S615 the patient takes action in accordance with the healthcare provider's analysis, for example, cleaning the wound using a specified antiseptic material.

Although the embodiment depicted in FIG. 12 provides for evaluation of the patient's wound by a healthcare provider, it will be appreciated that such review could in whole or in part automatically. That is, a computer program could be provided which analyzes the wound taking into account factors such as wound size, coloration, appearance and so forth. In situations where the program cannot reach a conclusive diagnosis, the program could refer its findings to a healthcare practitioner for final analysis.

It will be appreciated by those skilled in the art that the foregoing embodiments of this invention shown in FIGS. 11A, 11B and 12 could be implemented by a suitable computer program carrying out the depicted operations. Information could be transferred to and from that system in known manner, for example, using keyboard inputs, displayed text, and uploaded and downloaded image files, all in accordance with known protocols.

Information obtained in the foregoing manner could be incorporated into the patient's medical records, where such information might later be used in such ways as monitoring how over time the patient's health has changed.

By way of non-limiting example, in connection with the aspects of this invention shown in FIG. 2, dietary or wound data could be included in the student information database 119 which stores profile information for each student. This way, the physician who checks in steps S11 and S19 of FIG. 3 on the diabetic patient's status will be able to study the patient's dietary habits and/or wound history.

By storing the patient's dietary information, it also will be possible to study their food consumption history, as well as to see whether they are becoming more accurate at estimating food portion size and nutritional value. This way, when the diabetic patient in step S127 of FIG. 4 checks their "personal scorecard" of health measurements, they also could obtain relevant dietary information. Patient's also could see whether they are becoming more or less prone to wounds.

The stored dietary information also could be used by the CDE to monitor the patient's eating habits. By way of non-limiting example, in step S325 shown in FIG. 6, when the CDE checks on the patient's health the CDE also would receive dietary information for the patient. The CDE could then evaluate whether (1) the patient is doing a satisfactory job of estimating portion size and nutritional value and (2) the patient is eating a healthy diet.

By way of non-limiting example, the present invention can be used for the "real-time", "delayed" and "near real-time" analysis of patient information. Also by way of non-limiting example, patient information can include general meal information, digital meal information, and blood chemistry readings such as blood glucose, A1C, and/or HbA1C.

"Real-time" analysis may be preferable, for example, when educating a newly-diagnosed diabetic patient how to care for themselves by judging the nutritional information of each meal and selecting the appropriate insulin dose. "Real-time" monitoring of a diabetic patient's health, whether with or without the digital imaging of meal, also may be appropriate where the patient does not exhibit stable blood readings, say, because they are in poor health.

"Delayed" analysis, again, either with or without the digital imaging of meals, could be used where the diabetic patient's blood glucose (or other significant readings) is generally stable and the patient has demonstrated good ability to care for themselves, and so general monitoring is appropriate.

"Near real-time" analysis may be preferable in other situations, say, where the diabetic patient's blood glucose is generally satisfactory, but subject to some variations, necessitating a higher level of attention. This arrangement also may be appropriate where the diabetic patient has only recently completed their basic diabetic education and the healthcare provider wishes to monitor them at an intermediate level of scrutiny.

As a further example, patient information could be used to analyze data once a week, the information then being sent back to the patient.

Another way the present invention could be used is as an intensive course of daily reviews sessions, say, for 1–2 weeks, or 5–10 sessions. Following such an initial course of education, the patient would then be able to manage on their own.

It will be understood that additional levels of analysis could be provided.

Figure 9:
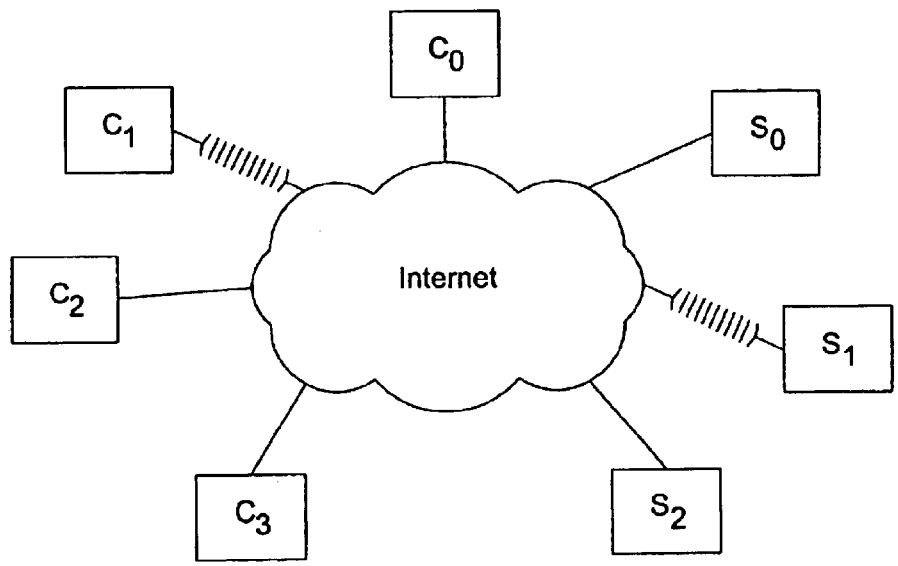
FIG. 9 is a schematic view showing a number of client and server computers communicating in known manner via the Internet.

Since the present invention is meant in part to be used over the Internet, various aspects of operation via the Internet will now be described with reference to FIG. 9. FIG. 9 is a schematic view depicting a number of client computers C0, C1, C2 and C3 and server computers S0, S1 and S2 all connected to the Internet. Client C1 and server S1, it should be noted, are joined to the Internet by wireless connections.

Among the types of data which can be sent between the computers is HTML data (hypertext mark-up language). HTML data can integrate both text and images. By way of non-limiting example, webpages can take the form of HTML data.

HTML data is typically transferred from a provider to a recipient. When this transfer takes place over a network, the content provider uses one or more server computers each having the appropriate server software to respond to requests for data, and the recipient employs a computer having the appropriate client software to send requests for data and receive and process responses to those requests.

Users typically exchange data, including HTML data, over the Internet using Internet browser software. Examples of browsers include Netscape Navigator® by Netscape Corporation, Internet Explorer® by Microsoft Corporation, and Opera from Opera Software A/S. Since the operation of browser software is generally known, such operation will not be described in detail.

Next, server and client computer equipment suitable for use with this invention will be described.

Figure 10:
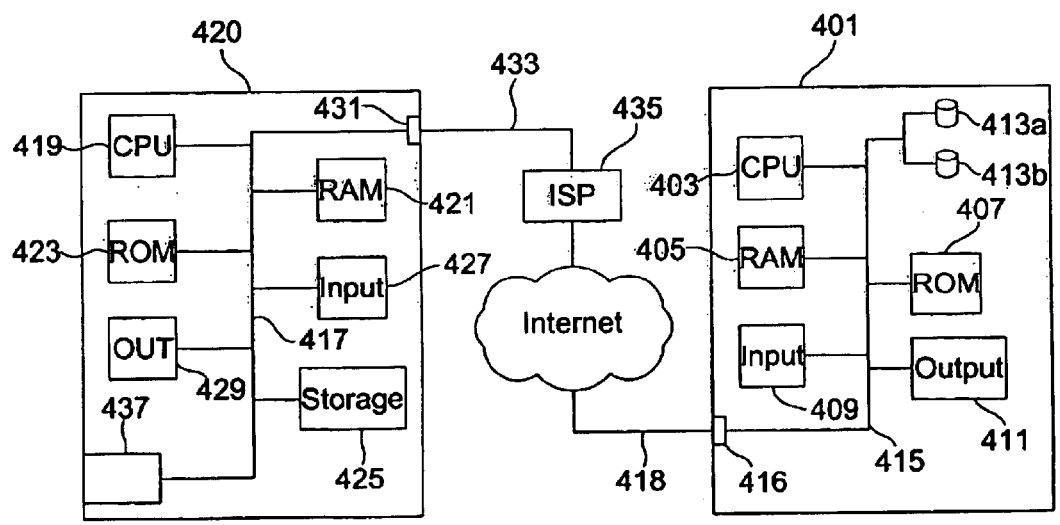
FIG. 10 is a schematic view showing various components of both client and server computers.

As depicted in FIG. 10, server 401 has a number of components, each of which will be described hereafter, connected to a bus 415. Bus 415 serves to relay commands and data between various components.

Central processing unit (CPU) 403 serves to control the internal operation of the server 401. Read-only memory (ROM) 407 is a non-volatile memory device which stores programs and data used by the CPU 403 as the server 401 starts up. Random access memory (RAM) 405 is a memory device which contains programs and data used by the CPU 403 during routine operation of server 401. Commands from an operator (not shown) are sent to the server 401 through an input device 409, which could by way of non-limiting example be a keyboard or a pointing device such as a "mouse" or trackball. Server 401 displays information through output 411. Output 411 can, for example, be a video monitor or a printer. Operating program and data files can be stored on an operation drive 413a, and data to be sent out from the server 401 to users can be stored on a content drive 413b. Drives 413a and 413b are preferably magnetic disk drives. The use of different drives 413a and 413b to store the operating programs and data separately from the content data is thought to be preferable because it facilitates the simultaneous reading of such operating information and content data. Moreover, although FIG. 10 depicts the use of two separate drives 413a and 413b, additional drives also could be provided. Alternatively, a single drive could be used.

Various types of data can be stored on server 401 for transmission over the Internet to users. Such data could, by way of non-limiting example, take the form of HTML (hypertext mark-up language) web pages, images, text, programs, audio and video files. The server 401 can therefore function as a data source.

Server 401 has a data port 416 through which the server 401 can exchange data over the Internet with external computers such as client computer 420. By way of non-limiting example, the data port 416 could be a cable modem, telephony modem or network connection. Data port 416 is connected to the Internet by data line 418, which by way of non-limiting example could be a coaxial cable, a telephone line, or an optical fiber, or any type of such connector now known or hereafter developed. Data line 418 also could be a wireless connection such as a satellite link.

In known fashion, server 401 has a unique IP (Internet protocol) address which identifies the server and distinguishes it from all other computers on the Internet.

Data is exchanged between server 401 and the Internet in accordance with pre-established protocols. Requests for data from users and the data sent in response can be exchanged using TCP/IP (Transmission Control Protocol/Internet Protocol), UDP (User Datagram Protocol), or other protocols.

Next, client computer 420 will be described with reference to FIG. 10.

In the same manner as server 401, client computer 420 has a unique IP (Internet protocol) address which identifies the client computer 420 and distinguishes it from all other computers on the Internet. The client computer's address can be either static or dynamic.

Client computer 420 includes a bus 417 through which commands and data flow between the client computer's different components. Central processing unit (CPU) 419 controls internal operation of the client 420. Programs and data used by the CPU 419 during start-up are stored in a read-only memory (ROM) 423. ROM 423 is preferably a non-volatile memory device. A random access memory (RAM) 421 is another memory device and this device contains programs and data that are used by the CPU 403 during routine operation of client 420. Storage device 425, commonly a magnetic disk drive, contains programs and data used by the client 420 during operation. Such programs include client software which enables the client 420 to communicate with the server 401 over the Internet.

Commands are sent to the client 420 by an operator (not shown) using an input device 427, which could by way of non-limiting example be a keyboard or a pointing device such as a "mouse" or trackball. Output 429 is provided to display information from the client 420, and can, for example, be a video monitor or a printer. The information displayed may related to the operating status of the client 420 or be controlled by programs running on the client 420.

A removable storage device 437 can accept, read, and optionally record data on removable media (not shown). By way of non-limiting example, the removable media used by the removable storage device 437 could be a magnetic floppy disk, compact disc (CD) device, a digital video disc (DVD) or a memory card device. Also by way of non-limiting example, the removable storage device 437 can be used to load programs from removable media onto the client 420, or save programs and data from the client 420 onto removable media.

Client 420 can exchange data with external sources such as server 401 via a data port 431. Where data is to be exchanged over the Internet, data port 43 1, which by way of non-limiting example could be a cable modem, telephony modem or network connection, is connected to a data line 433, which by way of non-limiting example could be a coaxial cable, a telephone line, or an optical fiber. Data line 433 also could be a wireless connection such as a satellite link.

Client 420 exchanges data over the Internet through an Internet Service Provider ("ISP") 435. When client 420 receives data from an external data source, client 420 functions as a data recipient. Data passes over data line 433 between the ISP 435 and the data port 431. The ISP 435 is itself connected to the Internet in a known manner which need not be discussed herein.

Client 420 could, by way of example only, be a personal computer. Alternatively, the client 420 could be a remote terminal which is connected to a central mainframe computer, a WebTV® unit, a Web-enabled cellular phone, a Web-enabled personal organizer such as a Palm Pilot®, or an Internet appliance, a low-cost device which eliminates certain of a computer's components, such as the hard disk drive.

As shown in FIG. 10, data can be sent from server 401 through data port 416 to data line 418. The data then passes through the Internet to the ISP 435. ISP 435 sends the data to the client 420 over data line 433 to data port 431.

Since data transfer takes place over the Internet, data is transmitted between the server 401 and client 420 using Internet transfer protocols such as transfer control protocol and Internet protocol (TCP/IP). Such protocols are themselves known and need not be described in detail herein.

Although the explanation of this invention describes its use in connection with the Internet, this invention is not intended to be limited thereto. The present invention also could be adapted for use over any other known or future developed networks. By way of non-limiting example, this invention could also be used over an Ethernet local area network.

Likewise, although the foregoing explanation of the preferred embodiment of this invention discusses the transfer of medical and educational information, this invention is not to be limited thereto. It is envisioned that the concepts taught herein could be applied to the transmission of any type of educational information over a computer network.

Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall there between. In particular, this invention should not be construed as being limited to the dimensions, proportions or arrangements disclosed herein.

What is claimed is:

1. A method or providing a patient with an analysis result which the patient can use to determine a dosage of a drug for self-administration comprising:

(a) gathering information which affects the dosage comprising information related to an item of food that may be eaten by a patient, the gathering being performed by the patient;

(b) automatically forwarding the information to an advisor, computer system, or combination thereof, which analyzes the information to obtain an analysis result; and (c) sending the analysis result to the patient, whereby the patient can determine the dosage using the analysis result and wherein the analysis result optionally comprises a portion for the item of food.

2. The method of claim 1, wherein the step of gathering information comprises obtaining a photograph of the item of food.

3. The method of claim 2, wherein the photograph is a digital image.

4. The method of claim 2 wherein the photograph shows at least a part of a meal to be eaten by the patient.

5. The method of claim 2, wherein the step of gathering information further comprises obtaining the patient's estimate of the size of the item of food.

6. The method of claim 2, wherein the step of gathering information is performed using a digital camera.

7. The method of claim 6, wherein the digital camera is a part of a device used by the patient for self-monitoring one or more physical conditions relevant to the patient's health.

8. The method of claim 7, wherein the device is a blood glucose monitor.

9. The method of claim 1, wherein the analysis result comprises a portion size for the item.

10. The method of claim 9, wherein the analysis result indicates that the patient should not eat the item of food.

11. The method of claim 1 wherein the patient suffers from diabetes and the dosage reflects an amount of insulin.

12. The method of claim 1, further comprising the step of storing the analysis result for use in evaluation of the patient, education of the patient, or both.

13. The method of claim 1, wherein at least one of the forwarding of the information and the sending of the analysis result is performed using the Internet.

14. A method for providing a patient with an analysis result which the patient can use to determine a dosage of a drug for self-administration comprising performing steps (a)–(c) of claim 1 for more than one item of food in a meal.

15. A computer-readable storage medium comprising a program for performing the method of claim 1.

16. The method of claim 1, wherein the patient performs a self-analysis and the method comprises comparing the analysis result with the patient's self-analysis.

17. The method of claim 1, wherein the method comprises forwarding the information to an advisor that analyzes the information to obtain an analysis result.

18. The method of claim 1, wherein the analysis result indicates that the patient should take no dosage of the drug.

19. A system for providing a patient with an analysis result which the patient uses to determine a dosage of a drug for self-administration comprising:

a data input component that receives from the patient gathered information that affects the dosage and that comprises information related to an item of food;

a data transfer component which transfers the information gathered by the patient to an advisor, a computer system, or combination thereof that analyzes the information to obtain the analysis result; and a data output component that automatically sends the analysis result to the patient.

20. The system of claim 19, wherein the information gathered by the patient and the analysis result are transferred using the Internet.

21. The system of claim 19, wherein the system comprises a computer program that analyzes the information to obtain the analysis result.

* * * * *